(12) United States Patent
Oliyai et al.

(10) Patent No.: US 10,857,102 B2
(45) Date of Patent: Dec. 8, 2020

(54) THERAPEUTIC COMPOSITIONS COMPRISING RILPIVIRINE HCL AND TENOFOVIR DISOPROXIL FUMARATE

(75) Inventors: Reza Oliyai, Burlingame, CA (US); Lauren Wiser, Cupertino, CA (US); Mark Menning, San Francisco, CA (US)

(73) Assignees: Gilead Sciences, Inc., Foster City, CA (US); Janssen Sciences Ireland UC, Little Island (IE)

( * ) Notice: Subject to any disclaimer, the term of this patent is extended or adjusted under 35 U.S.C. 154(b) by 423 days.

(21) Appl. No.: 13/988,072

(22) PCT Filed: Nov. 18, 2011

(86) PCT No.: PCT/US2011/061515
§ 371 (c)(1),
(2), (4) Date: May 17, 2013

(87) PCT Pub. No.: WO2012/068535
PCT Pub. Date: May 24, 2012

(65) Prior Publication Data
US 2013/0243857 A1 Sep. 19, 2013

Related U.S. Application Data

(60) Provisional application No. 61/415,600, filed on Nov. 19, 2010.

(51) Int. Cl.
*A61K 31/505* (2006.01)
*A61K 31/513* (2006.01)
*A61K 31/675* (2006.01)
*A61K 9/24* (2006.01)

(52) U.S. Cl.
CPC ............ *A61K 9/209* (2013.01); *A61K 31/505* (2013.01); *A61K 31/513* (2013.01); *A61K 31/675* (2013.01)

(58) Field of Classification Search
CPC .... A61K 9/209; A61K 31/505; A61K 31/513; A61K 31/675
See application file for complete search history.

(56) References Cited

U.S. PATENT DOCUMENTS

| | | |
|---|---|---|
| 2008/0286344 A1 | 11/2008 | Darmuzey et al. |
| 2009/0143314 A1 | 6/2009 | Dahl et al. |
| 2009/0324729 A1 | 12/2009 | Koziara et al. |

FOREIGN PATENT DOCUMENTS

| | | |
|---|---|---|
| CN | 101222914 | 7/2008 |
| CN | 101778855 | 7/2010 |
| EP | 1632232 | 3/2006 |
| JP | 2007-520443 A | 7/2007 |
| JP | 2008511592 | 4/2008 |
| JP | 2008-543861 A | 12/2008 |
| JP | 2008-546705 A | 12/2008 |
| WO | WO 92/14743 | 9/1992 |
| WO | WO-03/016306 A1 | 2/2003 |
| WO | WO-03/045327 A2 | 6/2003 |
| WO | WO-03/045327 A3 | 6/2003 |
| WO | WO-2004/064845 A1 | 8/2004 |
| WO | WO-2005/021001 A1 | 3/2005 |
| WO | WO-2006/024668 | 3/2006 |
| WO | WO-2006/135932 A2 | 12/2006 |
| WO | WO-2006/135932 A3 | 12/2006 |
| WO | WO-2006/135933 A2 | 12/2006 |
| WO | WO-2006/135933 A3 | 12/2006 |
| WO | WO 2007/047371 | 4/2007 |
| WO | WO 2007/068934 | 6/2007 |
| WO | WO 2008/140461 | 11/2008 |
| WO | WO-2008/143500 A1 | 11/2008 |
| WO | WO 2009/037449 | 3/2009 |
| WO | WO 2009/106960 | 9/2009 |
| WO | WO-2009/135179 A2 | 11/2009 |
| WO | WO-2009/135179 A3 | 11/2009 |
| WO | WO-2010/091197 A2 | 8/2010 |
| WO | WO-2010/091197 A3 | 8/2010 |
| WO | WO-2011/035231 A1 | 3/2011 |
| WO | WO 2011/077100 | 6/2011 |
| WO | WO 2012/068535 | 5/2012 |

OTHER PUBLICATIONS

Australian Office Action dated Oct. 29, 2014, for Australian Patent Application No. 2011329642, filed on Nov. 18, 2011, three pages.
Chilean Opposition filed by Asociacion Industrial de Laboratorios Farmaceuticos AG (ASILFA) dated Aug. 11, 2014 against Chilean Patent Application No. 1402-2013, two pages.
Chilean Opposition filed by Laboratorios Recalcine S.A. dated Aug. 11, 2014 against Chilean Patent Application No. 1402-2013, four pages.
Chinese Office Action dated Aug. 26, 2014, for Chinese Patent Application No. 201180063666.6, filed on Nov. 18, 2011, nine pages.
Columbian Office Action dated Aug. 2014, for Columbian Patent Application No. 13130615, filed on Nov. 18, 2011, eight pages.
Ecuadorian Opposition filed by Association of Pharmaceutical Laboratories dated Aug. 5, 2014 against Ecudorian Patent Application No. SP201312700, fifteen pages.
Eurasian Office Action dated Jul. 8, 2014, for Eurasian Patent Application No. 201390651, filed on Nov. 18, 2011, three pages.
Japanese Office Action dated Jun. 27, 2014 for Japanese Patent Application No. 2013-540085, filed on Nov. 18, 2011, five pages.
O'Neil, M.J. et al. (2006). "Emtricitabine," in *Merck Index: An Encyclopedia of Chemicals, Drugs, and Biologicals*, No. 3565, 14th Edition, Merck Research Laboratories: Whitehouse Station, NJ., pp. 607.
O'Neil, M.J. et al. (2006). "Tenofovir," in *Merck Index: An Encyclopedia of Chemicals, Drugs and Biologicals*, No. 9146, 14th Edition, Merck Research Laboratories: Whitehouse Station, NJ., pp. 1573.
clinicaltrials.gov. (Oct. 25, 2012). "TMC278-TiDP6-C209: A Clinical Trial in Treatment Naive HIV-1 Patients Comparing TMC278 to Efavirenz in Combination with Tenofovir + Emtricitabine," located at <http://www.clinicaltrials.gov/ct2/show/NCT00540449?term=tmc278&rank=10>, last visited on Mar. 31, 2014, three pages.

(Continued)

*Primary Examiner* — Adam C Milligan
(74) *Attorney, Agent, or Firm* — Fish & Richardson P.C.

(57) ABSTRACT

The invention provides multilayer tablets that contain rilpivirine hydrochloride, emtricitabine, and tenofovir disoproxil fumarate. The tablets are useful for the treatment of HIV.

5 Claims, 9 Drawing Sheets

(56) References Cited

OTHER PUBLICATIONS

Collins, S. (Aug. 26, 2010). "Rilpivirine (TMC-278) vs Efavirenz in Treatment Naive Patients: Phase 3 Results," Antiretrovirals: Conference Reports HIV Treatment Bulletin, located at <http://i-base.info/htb/13816>, last visited on Nov. 8, 2013, two pages.

Levin, J. (Jul. 18, 2010). "Bioequivalence of the Co-Formulation of Emtricitabine/Rilpivirine/Tenofovir DF," located at <http://www.natap.org/2010/IAS/IAS_99.htm>, last visited on Nov. 8, 2013, five pages.

Mathias, A. et al. (Jul. 18, 2010). "Bioequivalence of the Co-Formulation of Emtricitabine/Rilpivirine/Tenofovir DF," XVIII International AIDS Conference, Vienna, Austria.

Costa Rican Opposition filed on Jan. 24, 2014 against Costa Rican Patent Application No. 20130293, filed on Nov. 18, 2011, ten pages.

International Search Report dated Feb. 16, 2012 for PCT Patent Application No. PCT/US2011/061515 filed on Nov. 18, 2011, four pages.

Peruvian Opposition filed on May 6, 2014 against Peruvian Patent Application No. 12142013, filed on Nov. 18, 2011, eight pages.

Written Opinion of the International Searching Authority dated Feb. 16, 2012 for PCT Patent Application No. PCT/US2011/061515 filed on Nov. 18, 2011, seven pages.

Vietnamese Office Action dated Aug. 16, 2013 for Vietnamese Patent Application No. 1-2013-01761 filed on Nov. 18, 2011, one page.

Vietnamese Office Action dated Apr. 29, 2014 for Vietnamese Patent Application No. 1-2013-01761 filed on Nov. 18, 2011, one page.

Pendela, M. et al. (2011). "LC Assay for a HIV Tablet Containing Emtricitabine, Tenofovir Disoproxil Fumarate and Rilpivirine," *Chromatographia* 73:439-445.

Columbian Office Action dated Feb. 3, 2015, for Columbian Patent Application No. 13130615, filed on Nov. 18, 2011, thirteen pages.

Ukrainian Office Action dated Feb. 3, 2015, for Ukrainian Patent Application No. A201306403, filed on Nov. 18, 2011, two pages.

Extended European Search Report dated Sep. 2, 2011, for European Patent Application No. 11153967.2, filed on Feb. 10, 2011, seven pages.

AIDSInfonet.org (Apr. 21, 2014). "Fact Sheet 471—Complera/Eviplera," located at <http://www.aidsinfonet.org/fact_sheets/view/471>, last visited on Aug. 21, 2015, 3 pages.

AIDSMeds (Sep. 23, 2011). "Complera Counterpart Eviplera Recommended for European Approval," located at <http://www.aidsmeds.com/articles/hiv_eviplera_europe_1667_21165.shtml>, last visited on Aug. 21, 2015, 1 page.

Atripla (Dec. 18, 2007). "EPAR Scientific Discussion," located at < http://www.ema.europa.eu/docs/en_GB/document_library/EPAR_-_Scientific_Discussion/human/000797/WC500028105.pdf>, last visited on Aug. 21, 2015, 48 pages.

Center for Drug Evaluation and Research (2011). Approval Package for Complera™, Gilead Sciences, Inc., 495 pages.

Center for Drug Evaluation and Research (2011). "Clinical Pharmacology and Biopharmaceuticals Review(s)," Gilead Sciences, Inc., 63 pages.

Cohen, C.J. et al. (Jul. 16, 2011). "Rilpivirine Versus Efavirenz with Two Background Nucleoside or Nucleotide Reverse Transcriptase Inhibitors in Treatment-Naïve Adults Infected with HIV-1 (THRIVE): A Phase 3, Randomised, Non-Inferiority Trial," *Lancet* 378(9787):229-237.

Cohen, C. et al. (Jul. 18-23, 2010). "Pooled Week 48 Efficacy and Safety Results from ECHO and THRIVE, Two Double-Blind, Randomised, Phase III Trials Comparing TMC278 Versus Efavirenz in Treatment-Naïve, HIV-1 Infected Patients," XVIII International AIDS Conference, Vienna, Austria, Abstract THLBB206, 2 pages.

Cohen, C. et al. (Jul. 18-23, 2010). "Pooled Week 48 Efficacy and Safety Results from ECHO and THRIVE, Two Double-Blind, Randomised, Phase III Trials Comparing TMC278 Versus Efavirenz in Treatment-Naïve, HIV-1 Infected Patients," XVIII International AIDS Conference, Vienna, Austria, Abstract THLBB206, PowerPoint Presentation, 14 pages.

Declaration of Mateja Novak Stagoj (Jun. 4, 2015), 11 pages.

Drugs@FDA—FDA Approved Drug Products (2015). "Complera," located at < http://www.accessdata.fda.gov/scripts/cder/drugsatfda/index.cfm?fuseaction=Search.DrugDetails>, last visited on Aug. 21, 2015, 2 pages.

European Medicines Agency (Sep. 22, 2011). "Assessment Report—Eviplera," located at < http://www.ema.europa.eu/docs/en_GB/document_library/EPAR_-_Public_assessment_report/human/002312/WC500118803.pdf>, last visited on Aug. 21, 2015, 90 pages.

Garvey, L. et al. (Jul. 2009). "Rilpivirine: A Novel Non-Nucleoside Reverse Transcriptase Inhibitor," *Expert Opin. Investig. Drugs* 18(7):1035-1041.

Gilead Press Release (2013). "U.S. FDA Approves Gilead's Once-Daily Single Tablet HIV-1 Regimen Complera® for Patients Switching from a Stable Regimen," located at < http://www.gilead.com/news/press-releases/2013/12/us-fda-approves-gileads-oncedaily-single-tablet-hiv1-regimen-complera-for-patients-switching-from-a-stable-regimen>, last visited on Aug. 19, 2015, 4 pages.

Gilead Press Release (Sep. 23, 2011). "European CHMP Adopts Positive Opinion for Eviplera®, a Once-Daily Single-Tablet Regimen for the Treatment of HIV Infection," located at < http://www.gilead.com/news/press-releases/2011/9/european-chmp-adopts-positive-opinion-for-eviplerar--a-oncedaily-singletablet-regimen-for-the-treatment-of-hiv-infection>, last visited on Aug. 21, 2015, 2 pages.

HIV Treatment Bulletin (Dec. 1, 2011). "Rilpivirine (Edurant) and Rilpivirine/FTC/Tenofovir FDC (Eviplera) Approved in Europe," located at < http://i-base.info/htb/15936>, last visited on Aug. 21, 2015, 4 pages.

Molina, J.M. et al. (Jul. 16, 2011). "Rilpivirine Versus Efavirenz with Tenofovir and Emtricitabine in Treatment-Naïve Adults Infected with HIV-1 (ECHO): A Phase 3 Randomised Double-Blind Active-Controlled Trial," *Lancet* 378(9787):238-246.

Ritschel, W.A. et al. (2002). "Die Tablette," Editio Cantor Verlag Aulendorf, $2^{nd}$ Edition, p. 23.

Schrijvers, R. et al. (Jul. 16, 2011). "Rilpivirine: A Step Forward in Tailored HIV Treatment," *Lancet* 378(9787):201-203.

Truvada (Nov. 22, 2005). "EPAR Scientific Discussion," located at <http://www.ema.europa.eu/docs/en_GB/document_library/EPAR_-_Scientific_Discussion/human/000594/WC500043716.pdf>, last visited on Aug. 21, 2015, 28 pages.

United States Securities and Exchange Commission (2014) Form 10-K: Gilead Sciences, Inc., located at < http://www.gilead.com/ar2014/assets/img/gileadsciences_10k_20150225.pdf, last visited on Aug. 21, 2015, pp. 1 and 11, 2 pages.

Ritschel, W.A. et al. (2002). "The Tablet: Handbook of Development, Manufacturing and Quality Assurance," $2^{nd}$ Edition, p. 23 (with English Translation).

African Regional Office Action dated Jul. 2, 2015, for African Regional Patent Application No. AP/p/2013/006931, filed on Nov. 18, 2011, six pages.

Taiwanese Office Action dated Nov. 27, 2015, for Taiwanese Patent Application No. 100142311, filed on Nov. 18, 2011, twelve pages.

Japanese Office Action dated Feb. 10, 2016, for Japanese Patent Application No. 2015-085594, filed on Apr. 20, 2015, nine pages.

Australian Office Action dated Nov. 30, 2015, for Australian Patent Application No. 2011329642, filed on Nov. 18, 2011, three pages.

Chilean Office Action dated Jul. 28, 2016, for Chilean Patent Application No. 1402-2013, filed on Nov. 18, 2011, ten pages.

Israel Office Action dated Jul. 28, 2016 for Israel Patent Application No. 226300 filed on Nov. 18, 2011, six pages.

Japanese Office Action dated Sep. 5, 2016 for Japanese Patent Application No. 2015-085594, filed on Nov. 18, 2011, ten pages.

Malaysian Office Action dated Jun. 30, 2016, for Malaysian Patent Application No. PI2013001825, filed on Nov. 18, 2011, three pages.

Mexican Office Action dated Jun. 10, 2016, for Mexican Patent Application No. MX/a/2013/005669, filed on Nov. 18, 2011, five pages.

(56) References Cited

OTHER PUBLICATIONS

Mexican Office Action dated Nov. 26, 2015, for Mexican Patent Application No. MX/a/2013/005669, filed on Nov. 18, 2011, six pages.
Philippines Office Action dated Sep. 29, 2016 for Philippines Patent Application No. 12013501002 filed on Nov. 18, 2011, four pages.
Australian Office Action in Australian Application No. 2016208417, dated Mar. 17, 2017, 4 pages.
Canadian Office Action in Canadian Application No. 2818097, dated Feb. 8, 2017, 3 pages.
Eurasian Office Action in Eurasian Application No. 201691695, dated Mar. 7, 2017, 2 pages (with English translation).
International Preliminary Report on Patentability in International Application No. PCT/US2011/061515, dated May 21, 2013, 8 pages.
Philippines Office Action in Philippines Application No. 12013501002, dated Nov. 22, 2016, 2 pages.
Vietnamese Office Action in Vietnamese Application No. 1201301761, dated Dec. 23, 2016, 3 pages (with English translation).
"Edurant 25mg Fil-coated tablets," Jan. 2001 [retrieved on Dec. 13, 2017], retrieved from: http://www.onmeda.de/Medikament/EDURANT+25mg+Filmtabletten--wirkung+dosienung.html 6 pages.
Canadian Office Action in Canadian Application No. 2818097, dated Nov. 8, 2017, 2 pages.
Chilean Office Action in Chilean Application No. 201031402, dated May 17, 2017, 19 pages (with English translation).
Eurasian Patent Office Search Report for Eurasian Patent Application No. 201691695, dated Nov. 30, 2017, 4 pages (with English Translation).
Israel Office Action Received Sep. 18, 2017 in Israeli Patent Application No. 226300 9 pages (with English translation).
Australian Office Action in Australian Application No. 2016208417, dated Mar. 13, 2018, 4 pages.
CHMP, "Guideline on the Investigation of Bioequivalence," European Medicines Agency: Committee for Medicinal Products for Human Use (CHMP), 2010, 27 pages.
Costa Rican Office Action issued in Patent Application No. 2013-0293, dated Mar. 16, 2018, 16 pages (with English translation).
EPO Communication re Notice of Appeal to Opponents in European Application No. 11791161, dated Apr. 12, 2018, 2 pages.
EPO Communication re Notice of Appeal to proprietor in European Application No. 11791161, dated Apr. 12, 2018, 1 page.
EPO Final Grounds of Appeal in European Application No. 11791161, dated Apr. 6, 2018, 18 pages.
EPO Grounds of Appeal in European Application No. 1179161, dated Apr. 9, 2018, 18 pages.
EPO Opposition Response in European Application No. 11791161, dated Feb. 29, 2016, 11 pages.
EPO Interlocutory Decision in Opposition Proceedings in European Application No. 11791161, dated Nov. 29, 2017, 21 pages.
EPO Preliminary Opinion of the Opposition Division in European Application No. 11791161, dated Feb. 6, 2017, 6 pages.
Excerpt from Dahl and Yang's Employment Agreements, submitted to EPO on Feb. 29, 2016, 1 page.
Gilead Sciences, Inc., "U.S. Food and Drug Administration Approves Gilead Sciences' Complera(TM), a New Complete Once-Daily, Single-Tablet Regimen for HIV-1 Infection in Treatment-Naïve Adults," Gilead Sciences Inc. Press Release, Aug. 10, 2011, retrieved on Jun. 10, 2018, URL <http://www.gilead.com/news/press-releases?year=2011>, 6 pages.
India Office Action in India Application No. 4424/DELNP/2013, dated Jan. 23, 2018, 7 pages (with English translation).
Korean Office Action in Korean Application No. 10-2013-7015719, dated Jan. 5, 2018, 3 pages (English translation).
Mathias et al., "Bioequivalence of the Emtricitabine/Rilpivirine/Tenofovir Disoproxil Fumarate Single Tablet Regimen," J Bioequivalence & Bioavailability, 2012, 4(7): 100-105.
Mexican Office Action in Mexican Application No. MX/a/2017/005554, 2 pages (English Translation Only).
PCT Request in Application No. PCT/US2011/61515, dated May 24, 2012, 4 pages.
USPTO Assignment in U.S. Appl. No. 61/415,600, dated Jul. 13, 2011, 3 pages.
USPTO Corrected Filing Receipt in U.S. Appl. No. 61/415,600, dated Feb. 3, 2012, 3 pages.
USPTO Request to Correct Inventorship in U.S. Appl. No. 61/415,600, dated Jul. 21, 2011, 1 page.
Voigt, "7.4 Bioaquivalenz," Pharmazeutische Technologie, 2006, 219-220 (with English translation).
CN Office Action in Chinese Appln. No. 2016109001831, dated Jul. 31, 2018, 25 pages (with English translation).
CR Office Action in Costa Rican Appln. No. 2013-0000293, dated Aug. 23, 2018, 24 pages (with English translation).
AU Office Action in Australian Appln. No. 2018202635, dated Nov. 30, 2018, 4 pages.
PE Office Action in Peruvian Appln. No. 2828-2016, dated Oct. 11, 2018, 2 pages (with English translation).
SV Office Action in Salvadoran Appln. No. E44632013, dated Sep. 6, 2018, 10 pages (with English translation).
Balasubramaniam et al, "Effect of Superdisintegrants on Dissolution of Cationic Drugs," Dissolution Technologies, May, 2008, 18-25.
CR Office Action in Costa Rican Appln. No. 2013-0000293, dated Feb. 26, 2019, 17 pages (with English translation).
European Search Report in Appln. No. 14183494.5-1112, dated May 10, 2019, 5 pages.
Aulton, "Pharmaceutics: the science of dosage form design," Elsevier Science Limited, 2002, p. 411, col. 2.
Costa Rica Notice of Appeal in CR Appln. No. 2013-0293, dated Nov. 14, 2019, 16 pages (English translation only).
Ecuadorian Office Action in EC Appln. No. SP-13-12700, dated Dec. 9, 2019, 12 pages.
Egyptian Office Action in EG Appln. No. PCT8442013, dated Nov. 19, 2019, 5 pages.
Koo, "Manufacturing Process Considerations for Fixed-Dose Combination Drug Products," American Pharmaceutical Review, 2010, 5 pages.
Chinese Office Action dated May 6, 2015, for Chinese Patent Application No. 201180063666.6, filed on Nov. 18, 2011, seven pages.
Eurasian Office Action dated Jun. 15, 2015, for Eurasian Patent Application No. 201390651, filed on Nov. 18, 2011, three pages.
European Opposition filed by LEK Pharmaceuticals d.d. on Jun. 9, 2015, against European Patent Application No. 11 791 161.0, thirty-two pages.
European Opposition filed by HGF Limited on Jun. 10, 2015, against European Patent Application No. 11 791 161.0, twenty-six pages.
Japanese Office Action dated Jan. 19, 2015, for Japanese Patent Application No. 2013-540085, filed on Nov. 18, 2011, three pages.
New Zealand Office Action dated Jun. 9, 2015, for New Zealand Patent Application No. 610729, filed on Nov. 18, 2011, two pages.
Trinidad & Tobago Office Action dated Feb. 2, 2015, for Trinidad & Tobago Patent Application No. TTA201300050, filed on Nov. 18, 2011, one page.
Argentinean Office Action in Argentinian Appln. No. P110104318, dated Jul. 7, 2020, 12 pages (with English translation).
Egyptian Office Action in EG Appln. No. PCT 844/2013, dated Aug. 16, 2020, 4 pages (English translation only).

THERAPEUTIC COMPOSITIONS COMPRISING RILPIVIRINE HCL AND TENOFOVIR DISOPROXIL FUMARATE

PRIORITY OF INVENTION

This application claims priority to U.S. Provisional Application No. 61/415,600 that was filed on 19 Nov. 2010. The entire content of this provisional application is hereby incorporated herein by reference.

BACKGROUND OF THE INVENTION

Rilpivirine HCl (RPV), an investigational new drug for the treatment of HIV infection, has the following formula I:

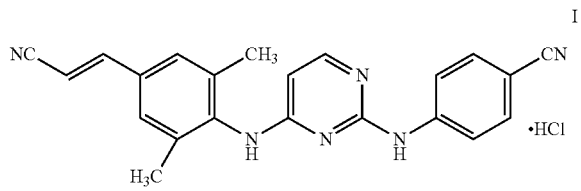 [SMILES: Cc1cc(/C=C/C#N)cc(C)c1Nc1ccnc(Nc2ccc(C#N)cc2)n1 ; Cl]

It is a second-generation non-nucleoside reverse transcriptase inhibitor (NNRTI) with longer half-life and better side-effect profile compared with other commercial NNRTIs, including efavirenz.

Emtricitabine (FTC) is a nucleoside reverse transcriptase inhibitor having the following formula II:

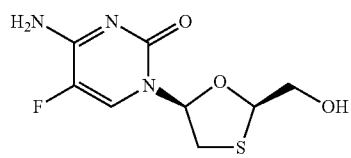

Emtricitabine is present as an active ingredient in EMTRIVA® (emtricitabine) capsules, TRUVADA® (emtricitabine and tenofovir DF) tablets, and ATRIPLA® (efavirenz, emtricitabine, and tenofovir DF) tablets, which are marketed for the treatment of HIV infection. Tenofovir disoproxil fumarate (Tenofovir DF or TDF) is a reverse transcriptase inhibitor having the following formula III:

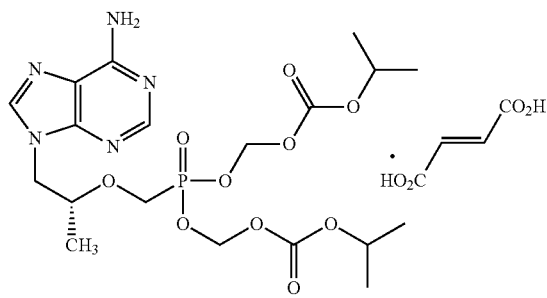

Tenofovir DF is also present as an active ingredient in VIREAD® (tenofovir DF) tablets, TRUVADA® (emtricitabine and tenofovir DF) tablets, and ATRIPLA® (efavirenz, emtricitabine, and tenofovir DF) tablets.

A combination of rilpivirine HCl, emtricitabine, and tenofovir DF is currently being investigated in clinical studies for the treatment of HIV (for example TMC278-TiDP6-C209: A Clinical Trial in Treatment Naive HIV-1 Patients Comparing TMC278 to Efavirenz in Combination With Tenofovir+Emtricitabine at www.clinicaltrials.gov/ct2/show/-NCT00540449?term=TMC278&rank=10. In the current clinical studies this combination is administered as two tablets: one tablet containing rilpivirine HCl, and the second tablet being the commercial product TRUVADA® (emtricitabine 200 mg/tenofovir DF 300 mg).

A fixed-dose combination product containing rilpivirine HCl, emtricitabine, and tenofovir DF in a solid oral dosage form would be desirable. Such a fixed-dose combination would provide patient dosing convenience for once daily administration. Clinical studies have demonstrated high levels of compliance and treatment satisfaction, with simple once-daily highly active antiretroviral therapies (HAART), resulting in durable suppression of HIV-1 RNA.

International patent application publication number WO 2005/021001 discusses a co-wet granulation process for preparing a single tablet that comprises rilpivirine HCl, emtricitabine, and tenofovir DF. Unfortunately chemical stability of tenofovir DF is affected in the presence of rilpivirine HCl. Thus, the formulation provided by the co-wet granulation process discussed in WO 2005/021001 is not ideal for human clinical use.

There is currently a need for a fixed-dose combination product containing rilpivirine HCl, emtricitabine, and tenofovir DF. Ideally, the fixed-dose combination product will provide suitable chemical stability for the active ingredients and will be of an acceptable size as a unit dose form. Additionally, it would be beneficial for the fixed-dose form to produce human plasma concentrations of each of the three agents that are equivalent to the plasma concentrations produced by the administration of the individual agents.

SUMMARY OF THE INVENTION

Applicant has discovered a single multilayer formulation of rilpivirine HCl, emtricitabine, and tenofovir DF that provides suitable chemical stability for the active ingredients as well as plasma concentrations of the three agents that are equivalent to the plasma concentrations produced by the administration of Emtriva (emtricitibine 200 mg) capsules, Viread (tenofovir DF 300 mg) tablets, and a third tablet containing rilpivirine HCl that is currently being evaluated in clinical trials. Additionally, the single multilayer formulations identified by Applicant provide a similar drug exposure, as measured by the plasma concentration area under the curve (AUC), when dosed with and without food as compared to the dosing of the individual components with food. Dosing the individual components without food showed a decrease in rilpivirine exposure (AUC) by 21% compared to dosing the individual components with food. Having a restriction of dosing with food only can complicate the dosing regimen and compromise patient dosing compliance.

Accordingly, in one embodiment the invention provides a tablet comprising a first layer and a second layer wherein; a) the first layer comprises rilpivirine HCl; b) the second layer comprises tenofovir DF; and c) the tablet further comprises emtricitabine.

In one embodiment the invention provides a method for treating HIV infection in a human comprising administering to the human a tablet of the invention, wherein rilpivirine AUC achieved following administration to the human when fed is no more than about 25% greater than rilpivirine AUC achieved when administered to the human when fasted.

In one embodiment the invention provides a method for treating HIV infection in a human comprising administering to the human a tablet of the invention, wherein rilpivirine Cmax achieved following administration to the human when fed is no more than about 25% greater than rilpivirine Cmax achieved when administered to the human when fasted.

In one embodiment the invention provides a tablet of the invention for use in the prophylactic or therapeutic treatment of an HIV infection, wherein rilpivirine AUC achieved following administration to the human when fed is no more than about 25% greater than rilpivirine AUC achieved when administered to the human when fasted.

In one embodiment the invention provides a tablet of the invention for use in the prophylactic or therapeutic treatment of an HIV infection, wherein rilpivirine $C_{max}$ achieved following administration to the human when fed is no more than about 25% greater than rilpivirine $C_{max}$ achieved when administered to the human when fasted.

In one embodiment the invention provides a tablet of the invention for use in the prophylactic or therapeutic treatment of an HIV infection.

In one embodiment the invention provides the use of a tablet as described in any one of claims for preparing a medicament for treating HIV infection in a human.

The invention also provides processes described herein for preparing tablets of the invention as well as novel intermediate mixtures that are useful for preparing tablets of the invention.

The tablets of the invention represent an advance in the development of multi-drug therapy for the treatment of viral infections such as HIV.

DETAILED DESCRIPTION

Figure 1:
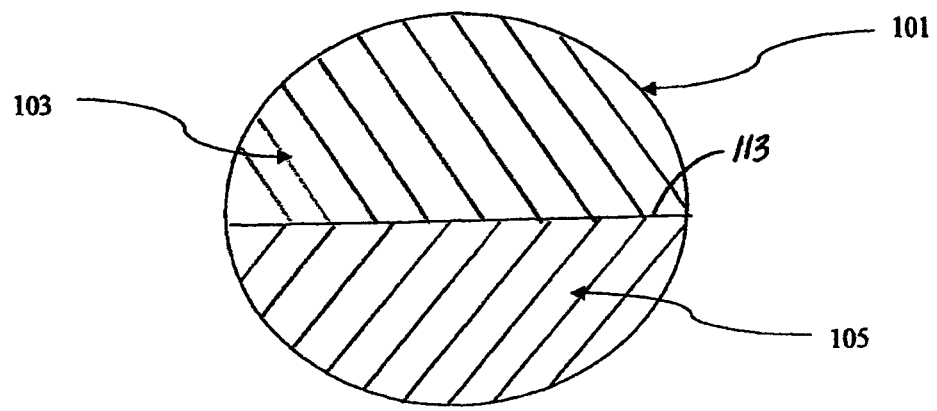
FIG. 1. Illustrates a tablet of the invention.

As used herein with respect to the methods of the invention, administration to a human when "fed" means administering a tablet of the invention to a human within 5 minutes of the human consuming a standardized meal of about 300 to 600 calories and about 10 to about 15 grams of fat.

As used herein with respect to the methods of the invention, administration to a human when "fasted" includes administering a tablet of the invention to a human who has not consumed food in the time period from about 8 hours prior to administration of the tablet to about 4 hours after administration of the tablet.

As used herein, when a tablet of the invention comprises a layer that is "substantially free" of a given component it means that less than 5% of the total weight of the given component present in the tablet is found in that layer. In one embodiment of the invention when a tablet of the invention comprises a layer that is "substantially free" of a given component it means that less than 1% of the total weight of the given component present in the tablet is found in that layer.

Specific values listed below for ranges and terms are for illustration only; they do not exclude other values.

In one embodiment the invention provides a tablet wherein the second layer comprises the emtricitabine.

In one embodiment the invention provides a tablet which comprises 27.5±1.4 mg of rilpivirine HCl.

In one embodiment the invention provides a tablet which comprises 200±10.0 mg of emtricitabine.

In one embodiment the invention provides a tablet which comprises 300±15.0 mg of tenofovir DF.

In one embodiment of the invention the first layer further comprises one or more diluents, disintegrants, binders, or lubricants.

In one embodiment of the invention the total weight of the first layer in the tablet of the invention is 275±75 mg.

In one embodiment of the invention the total weight of the first layer in the tablet is greater than 225 mg.

In one embodiment of the invention the total weight of the first layer in the tablet of the invention is 275±50 mg.

In one embodiment the invention provides a tablet of the invention wherein the first layer comprises lactose monohydrate, povidone, croscarmellose sodium, polysorbate 20, microcrystalline cellulose, and magnesium stearate.

In one embodiment the invention provides a tablet of the invention wherein the first layer comprises a basifying agent. In one embodiment of the invention the basifying agent is selected from croscarmellose sodium, calcium carbonate, sodium hydroxide, aluminum oxide, alkali metal hydroxides (e.g. such as sodium hydroxide, potassium hydroxide and lithium hydroxide), alkaline earth metal hydroxides (e.g. calcium hydroxide, and magnesium hydroxide), aluminum hydroxide, dihydroaluminum, sodium carbonate, aluminum magnesium hydroxide sulfate, aluminum hydroxide magnesium carbonate, ammonium hydroxides, magnesium carbonate, magnesium stearate, piperazine, sodium acetate, sodium citrate, sodium tartrate, sodium maleate, and sodium succinate and mixtures thereof.

In one embodiment the invention provides a tablet of the invention wherein the first layer comprises croscarmellose sodium, and polysorbate 20.

In one embodiment the invention provides a tablet of the invention wherein the first layer comprises lactose monohydrate, povidone, croscarmellose sodium, polysorbate 20, microcrystalline cellulose, and magnesium stearate.

In one embodiment the invention provides a tablet of the invention wherein the second layer comprises microcrystalline cellulose and croscarmellose sodium.

In one embodiment the invention provides a tablet of the invention wherein the second layer comprises lactose monohydrate, pre-gelatinized starch, microcrystalline cellulose, croscarmellose sodium, and magnesium stearate.

In one embodiment the invention provides a tablet of the invention wherein the first layer is in contact with the second layer.

In one embodiment the invention provides a tablet of the invention that further comprises a third layer that is between and that separates the first layer and the second layer. In one embodiment the third layer comprises lactose monohydrate, or microcrystalline cellulose, or a mixture thereof.

In one embodiment the invention provides a tablet of the invention wherein the first layer is a film coating that covers the second layer.

In one embodiment the invention provides a tablet of the invention wherein the first layer is a polymeric film coating that completely covers the second layer.

In one embodiment the invention provides a tablet that further comprises a film coating. In one embodiment the film coating comprises 34±12 mg of Opadry II Purple 33G100000.

In one embodiment the invention provides a tablet wherein at least about 5.4 weight percent of the first layer is croscarmellose sodium and at least about 63.3 weight percent of the first layer is lactose monohydrate.

In one embodiment the invention provides a tablet wherein less than about 12.2 weight percent of the first layer is rilpivirine hydrochloride.

In one embodiment the invention provides a tablet wherein less than about 12 weight percent of the first layer is rilpivirine hydrochloride.

In one embodiment the invention provides a tablet wherein the first layer comprises 27.5±1.4 mg of rilpivirine hydrochloride and wherein the total weight of the first layer is at least about 230 mg.

In one embodiment the invention provides a tablet wherein the first layer comprises 27.5±1.4 mg of rilpivirine hydrochloride and wherein the total weight of the first layer is at least about 240 mg.

In one embodiment the invention provides a tablet wherein the first layer comprises 27.5±1.4 mg of rilpivirine hydrochloride and wherein the total weight of the first layer is at least about 250 mg.

In one embodiment the invention provides a tablet wherein the first layer comprises 27.5±1.4 mg of rilpivirine hydrochloride and wherein the total weight of the first layer is at least about 260 mg.

In one embodiment the invention provides a tablet wherein the first layer comprises 27.5±1.4 mg of rilpivirine hydrochloride and wherein the total weight of the first layer is at least about 270 mg.

In one embodiment the invention provides a tablet wherein the first layer comprises 27.5±1.4 mg of rilpivirine hydrochloride and wherein the total weight of the first layer is at least about 280 mg.

In one embodiment the invention provides a tablet wherein the first layer comprises 27.5±1.4 mg of rilpivirine hydrochloride and wherein the total weight of the first layer is at least about 290 mg.

In one embodiment the invention provides a tablet wherein the first layer comprises 27.5±1.4 mg of rilpivirine hydrochloride and wherein the total weight of the first layer is at least about 300 mg.

In one embodiment the invention provides a tablet wherein the first layer comprises 27.5±1.4 mg of rilpivirine hydrochloride and wherein the total weight of the first layer is at least about 230 mg and is less than about 325 mg.

In one embodiment the invention provides a tablet wherein the first layer comprises 27.5±1.4 mg of rilpivirine hydrochloride and wherein the total weight of the first layer is at least about 300 mg and is less than about 325 mg.

In one embodiment the invention provides a tablet wherein the first layer comprises 27.5±1.4 mg of rilpivirine hydrochloride and wherein the total weight of the first layer is at least about 290 mg and is less than about 310 mg.

In one embodiment the invention provides a tablet prepared as described herein.

In one embodiment the invention provides a tablet of the invention wherein the first layer comprises:

| Ingredient | Unit Formula for Tablets (mg/tablet) |
| --- | --- |
| Rilpivirine HCl | 27.5 ± 1.4 |
| Microcrystalline Cellulose | 60.0 ± 3 |
| Polysorbate 20 | 0.4 ± 0.02 |
| Croscarmellose Sodium | 16.1 ± 0.8 | and the second layer comprises:

| Ingredient | Unit Formula for Tablets (mg/tablet) |
| --- | --- |
| Emtricitabine | 200 ± 10 |
| Tenofovir DF | 300 ± 15 |
| Microcrystalline Cellulose | 150 ± 7.5 |
| Croscarmellose Sodium | 60 ± 3 |

In one embodiment the invention provides a tablet of the invention wherein the first layer comprises:

| Ingredient | Layer (% w/w) | Total Tablet (% w/w) | Unit Formula for Tablets (mg/tablet) |
| --- | --- | --- | --- |
| Rilpivirine HCl | 9.2 | 2.4 | 27.5 |
| Microcrystalline Cellulose | 20.0 | 5.2 | 60.0 |
| Lactose Monohydrate | 63.3 | 16.5 | 189.8 |
| Povidone | 1.1 | 0.3 | 3.3 |
| Polysorbate 20 | 0.1 | 0.03 | 0.4 |
| Croscarmellose Sodium | 5.4 | 1.4 | 16.1 |
| Magnesium Stearate | 1.0 | 0.3 | 3.0 | and the second layer comprises:

| Ingredient | Layer (% w/w) | Total Tablet (% w/w) | Unit Formula for Tablets (mg/tablet) |
| --- | --- | --- | --- |
| Emtricitabine | 23.5 | 17.4 | 200.0 |
| Tenofovir DF | 35.3 | 26.1 | 300.0 |
| Microcrystalline Cellulose | 17.6 | 13.0 | 150.0 |
| Lactose Monohydrate | 9.4 | 7.0 | 80.0 |
| Pregelatinized Starch | 5.9 | 4.3 | 50.0 |
| Croscarmellose Sodium | 7.1 | 5.2 | 60.0 |
| Magnesium Stearate | 1.2 | 0.9 | 10.0. |

In one embodiment the invention provides a tablet comprising a first layer that comprises:

| Ingredient | Layer (% w/w) | Total Tablet (% w/w) | Unit Formula for Tablets (mg/tablet) |
| --- | --- | --- | --- |
| Rilpivirine HCl | 9.2 | 2.4 | 27.5 |
| Microcrystalline Cellulose | 20.0 | 5.2 | 60.0 |
| Lactose Monohydrate | 63.3 | 16.5 | 189.8 |
| Povidone | 1.1 | 0.3 | 3.3 |
| Polysorbate 20 | 0.1 | 0.03 | 0.4 |
| Croscarmellose Sodium | 5.4 | 1.4 | 16.1 |
| Magnesium Stearate | 1.0 | 0.3 | 3.0 | a second layer that comprises:

| Ingredient | Layer (% w/w) | Total Tablet (% w/w) | Unit Formula for Tablets (mg/tablet) |
|---|---|---|---|
| Emtricitabine | 23.5 | 17.4 | 200.0 |
| Tenofovir DF | 35.3 | 26.1 | 300.0 |
| Microcrystalline Cellulose | 17.6 | 13.0 | 150.0 |
| Lactose Monohydrate | 9.4 | 7.0 | 80.0 |
| Pregelatinized Starch | 5.9 | 4.3 | 50.0 |
| Croscarmellose Sodium | 7.1 | 5.2 | 60.0 |
| Magnesium Stearate | 1.2 | 0.9 | 10.0 | and a third layer that is between and that separates the first layer and the second layer that comprises 150±8.0 mg of microcrystalline cellulose or lactose monohydrate, or a mixture thereof.

In one embodiment the invention provides a tablet of the invention wherein the first layer consists of:

| Ingredient | Layer (% w/w) | Total Tablet (% w/w) | Unit Formula for Tablets (mg/tablet) |
|---|---|---|---|
| Rilpivirine HCl | 9.2 | 2.4 | 27.5 |
| Microcrystalline Cellulose | 20.0 | 5.2 | 60.0 |
| Lactose Monohydrate | 63.3 | 16.5 | 189.8 |
| Povidone | 1.1 | 0.3 | 3.3 |
| Polysorbate 20 | 0.1 | 0.03 | 0.4 |
| Croscarmellose Sodium | 5.4 | 1.4 | 16.1 |
| Magnesium Stearate | 1.0 | 0.3 | 3.0 | and the second layer consists of:

| Ingredient | Layer (% w/w) | Total Tablet (% w/w) | Unit Formula for Tablets (mg/tablet) |
|---|---|---|---|
| Emtricitabine | 23.5 | 17.4 | 200.0 |
| Tenofovir DF | 35.3 | 26.1 | 300.0 |
| Microcrystalline Cellulose | 17.6 | 13.0 | 150.0 |
| Lactose Monohydrate | 9.4 | 7.0 | 80.0 |
| Pregelatinized Starch | 5.9 | 4.3 | 50.0 |
| Croscarmellose Sodium | 7.1 | 5.2 | 60.0 |
| Magnesium Stearate | 1.2 | 0.9 | 10.0. |

In one embodiment the invention provides a tablet comprising a first layer that consists of:

| Ingredient | Layer (% w/w) | Total Tablet (% w/w) | Unit Formula for Tablets (mg/tablet) |
|---|---|---|---|
| Rilpivirine HCl | 9.2 | 2.4 | 27.5 |
| Microcrystalline Cellulose | 20.0 | 5.2 | 60.0 |
| Lactose Monohydrate | 63.3 | 16.5 | 189.8 |
| Povidone | 1.1 | 0.3 | 3.3 |
| Polysorbate 20 | 0.1 | 0.03 | 0.4 |
| Croscarmellose Sodium | 5.4 | 1.4 | 16.1 |
| Magnesium Stearate | 1.0 | 0.3 | 3.0 | a second layer that consists of:

| Ingredient | Layer (% w/w) | Total Tablet (% w/w) | Unit Formula for Tablets (mg/tablet) |
|---|---|---|---|
| Emtricitabine | 23.5 | 17.4 | 200.0 |
| Tenofovir DF | 35.3 | 26.1 | 300.0 |
| Microcrystalline Cellulose | 17.6 | 13.0 | 150.0 |
| Lactose Monohydrate | 9.4 | 7.0 | 80.0 |
| Pregelatinized Starch | 5.9 | 4.3 | 50.0 |
| Croscarmellose Sodium | 7.1 | 5.2 | 60.0 |
| Magnesium Stearate | 1.2 | 0.9 | 10.0 | and a third layer that is between and that separates the first layer and the second layer that comprises 150±8.0 mg of microcrystalline cellulose or lactose monohydrate, or a mixture thereof.

In one embodiment the invention provides a tablet of the invention wherein the first layer is a film coating that covers the second layer and wherein the first layer comprises 27.5±1.4 mg of rilpivirine HCl; and the second layer comprises:

| Ingredient | Layer (% w/w) | Total Tablet (% w/w) | Unit Formula for Tablets (mg/tablet) |
|---|---|---|---|
| Emtricitabine | 23.5 | 17.4 | 200.0 |
| Tenofovir DF | 35.3 | 26.1 | 300.0 |
| Microcrystalline Cellulose | 17.6 | 13.0 | 150.0 |
| Lactose Monohydrate | 9.4 | 7.0 | 80.0 |
| Pregelatinized Starch | 5.9 | 4.3 | 50.0 |
| Croscarmellose Sodium | 7.1 | 5.2 | 60.0 and |
| Magnesium Stearate | 1.2 | 0.9 | 10.0. |

In one embodiment the invention provides a tablet of the invention wherein the first layer is a film coating that covers the second layer and wherein the first layer comprises 27.5±1.4 mg of rilpivirine HCl; and the second layer consists of:

| Ingredient | Layer (% w/w) | Total Tablet (% w/w) | Unit Formula for Tablets (mg/tablet) |
|---|---|---|---|
| Emtricitabine | 23.5 | 17.4 | 200.0 |
| Tenofovir DF | 35.3 | 26.1 | 300.0 |
| Microcrystalline Cellulose | 17.6 | 13.0 | 150.0 |
| Lactose Monohydrate | 9.4 | 7.0 | 80.0 |
| Pregelatinized Starch | 5.9 | 4.3 | 50.0 |
| Croscarmellose Sodium | 7.1 | 5.2 | 60.0 |
| Magnesium Stearate | 1.2 | 0.9 | 10.0. |

In one embodiment the invention provides a tablet of the invention wherein the first layer comprises:

| Ingredient | % w/w | Unit Formula for Tablets (mg/tablet) |
|---|---|---|
| Rilpivirine HCl | 2.4 | 27.5 |
| Microcrystalline Cellulose | 5.2 | 60.0 |
| Lactose Monohydrate | 16.5 | 189.8 |
| Povidone | 0.3 | 3.3 |
| Polysorbate 20 | 0.03 | 0.4 |
| Croscarmellose Sodium | 1.4 | 16.1 |
| Magnesium Stearate | 0.3 | 3.0 | and the second layer comprises:

| Ingredient | % w/w | Unit Formula for Tablets (mg/tablet) |
|---|---|---|
| Emtricitabine | 17.4 | 200.0 |
| Tenofovir DF | 26.1 | 300.0 |
| Microcrystalline Cellulose | 13.0 | 150.0 |
| Lactose Monohydrate | 7.0 | 80.0 |
| Pregelatinized Starch | 4.3 | 50.0 |
| Croscarmellose Sodium | 5.2 | 60.0 |
| Magnesium Stearate | 0.9 | 10.0. |

In one embodiment the invention provides a tablet comprising a first layer that comprises:

| Ingredient | % w/w | Unit Formula for Tablets (mg/tablet) |
|---|---|---|
| Rilpivirine HCl | 2.4 | 27.5 |
| Microcrystalline Cellulose | 5.2 | 60.0 |
| Lactose Monohydrate | 16.5 | 189.8 |
| Povidone | 0.3 | 3.3 |
| Polysorbate 20 | 0.03 | 0.4 |
| Croscarmellose Sodium | 1.4 | 16.1 |
| Magnesium Stearate | 0.3 | 3.0 | a second layer that comprises:

| Ingredient | % w/w | Unit Formula for Tablets (mg/tablet) |
|---|---|---|
| Emtricitabine | 17.4 | 200.0 |
| Tenofovir DF | 26.1 | 300.0 |
| Microcrystalline Cellulose | 13.0 | 150.0 |
| Lactose Monohydrate | 7.0 | 80.0 |
| Pregelatinized Starch | 4.3 | 50.0 |
| Croscarmellose Sodium | 5.2 | 60.0 |
| Magnesium Stearate | 0.9 | 10.0 | and a third layer that is between and that separates the first layer and the second layer that comprises 150±8.0 mg of microcrystalline cellulose or lactose monohydrate, or a mixture thereof.

In one embodiment the invention provides a tablet of the invention wherein the first layer consists of:

| Ingredient | % w/w | Unit Formula for Tablets (mg/tablet) |
|---|---|---|
| Rilpivirine HCl | 2.4 | 27.5 |
| Microcrystalline Cellulose | 5.2 | 60.0 |
| Lactose Monohydrate | 16.5 | 189.8 |
| Povidone | 0.3 | 3.3 |
| Polysorbate 20 | 0.03 | 0.4 |
| Croscarmellose Sodium | 1.4 | 16.1 |
| Magnesium Stearate | 0.3 | 3.0 | and the second layer consists of:

| Ingredient | % w/w | Unit Formula for Tablets (mg/tablet) |
|---|---|---|
| Emtricitabine | 17.4 | 200.0 |
| Tenofovir DF | 26.1 | 300.0 |
| Microcrystalline Cellulose | 13.0 | 150.0 |
| Lactose Monohydrate | 7.0 | 80.0 |
| Pregelatinized Starch | 4.3 | 50.0 |
| Croscarmellose Sodium | 5.2 | 60.0 |
| Magnesium Stearate | 0.9 | 10.0. |

In one embodiment the invention provides a tablet comprising a first layer that consists of:

| Ingredient | % w/w | Unit Formula for Tablets (mg/tablet) |
|---|---|---|
| Rilpivirine HCl | 2.4 | 27.5 |
| Microcrystalline Cellulose | 5.2 | 60.0 |
| Lactose Monohydrate | 16.5 | 189.8 |
| Povidone | 0.3 | 3.3 |
| Polysorbate 20 | 0.03 | 0.4 |
| Croscarmellose Sodium | 1.4 | 16.1 |
| Magnesium Stearate | 0.3 | 3.0 | a second layer that consists of:

| Ingredient | % w/w | Unit Formula for Tablets (mg/tablet) |
|---|---|---|
| Emtricitabine | 17.4 | 200.0 |
| Tenofovir DF | 26.1 | 300.0 |
| Microcrystalline Cellulose | 13.0 | 150.0 |
| Lactose Monohydrate | 7.0 | 80.0 |
| Pregelatinized Starch | 4.3 | 50.0 |
| Croscarmellose Sodium | 5.2 | 60.0 |
| Magnesium Stearate | 0.9 | 10.0 | and a third layer that is between and that separates the first layer and the second layer that comprises 150±8.0 mg of microcrystalline cellulose or lactose monohydrate, or a mixture thereof.

In one embodiment the invention provides a tablet of the invention wherein the first layer is a film coating that covers the second layer and wherein the first layer comprises 27.5±1.4 mg of rilpivirine HCl; and the second layer comprises:

| Ingredient | % w/w | Unit Formula for Tablets (mg/tablet) |
|---|---|---|
| Emtricitabine | 17.4 | 200.0 |
| Tenofovir DF | 26.1 | 300.0 |
| Microcrystalline Cellulose | 13.0 | 150.0 |
| Lactose Monohydrate | 7.0 | 80.0 |
| Pregelatinized Starch | 4.3 | 50.0 |
| Croscarmellose Sodium | 5.2 | 60.0 and |
| Magnesium Stearate | 0.9 | 10.0. |

In one embodiment the invention provides a tablet of the invention wherein the first layer is a film coating that covers the second layer and wherein the first layer comprises 27.5±1.4 mg of rilpivirine HCl; and the second layer consists of:

| Ingredient | % w/w | Unit Formula for Tablets (mg/tablet) |
|---|---|---|
| Emtricitabine | 17.4 | 200.0 |
| Tenofovir DF | 26.1 | 300.0 |
| Microcrystalline Cellulose | 13.0 | 150.0 |

-continued

| Ingredient | % w/w | Unit Formula for Tablets (mg/tablet) |
|---|---|---|
| Lactose Monohydrate | 7.0 | 80.0 |
| Pregelatinized Starch | 4.3 | 50.0 |
| Croscarmellose Sodium | 5.2 | 60.0 and |
| Magnesium Stearate | 0.9 | 10.0. |

The tablets of the invention may include one or more acceptable carriers. The carrier(s) should be "acceptable" in the sense of being compatible with the other ingredients of the formulation and physiologically innocuous to the recipient thereof. As used herein the term carrier includes excipients, glidants, fillers, binders, lubricant, diluents, preservatives, surface active agents, dispersing agents and the like. For example, see the Handbook of Pharmaceutical Excipients (APhA Publications, Washington, D.C.), which is hereby incorporated by reference herein in its entirety. The term carrier also includes agents such as sweetening agents, flavoring agents, coloring agents and preserving agents. Furthermore, these terms include the values mentioned herein as well as values in accord with ordinary practice.

The tablets of the invention can also comprise a film coating that covers a portion or all of the tablet. Film coatings are known in the art and can be composed of hydrophilic polymer materials, but are not limited to, polysaccharide materials, such as hydroxypropylmethyl cellulose (HPMC), methylcellulose, hydroxyethyl cellulose (HEC), hydroxypropyl cellulose (HPC), poly(vinylalcohol-co-ethylene glycol) and other water soluble polymers. Though the water soluble material included in the film coating of the present invention may include a single polymer material, it may also be formed using a mixture of more than one polymer. In one embodiment of the invention, the film coating comprises Opadry II Purple 33G100000, which is available from Colorcon.

The tablets of the invention may conveniently be presented in unit dosage form and may be prepared by any of the methods well known in the art of pharmacy. Techniques and formulations generally are found in Remington's Pharmaceutical Sciences (Mack Publishing Co., Easton, Pa.), which is hereby incorporated by reference herein in its entirety. Such methods include the step of bringing into association the active ingredient(s) with the carrier which constitutes one or more accessory ingredients.

A tablet can be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active agent or dispersing agent. Molded tablets may be made by molding in a suitable machine a mixture of the powdered active ingredient moistened with an inert liquid diluent. The tablets may optionally be coated, for example with a polymeric film coating that can optionally comprise a compound of formula I.

FIG. 1 shows a cross-section of a tablet (101) of the invention. The tablet includes a first layer (103) that comprises rilpivirine HCl. The tablet also includes a second layer (105) that comprises tenofovir DF. The first and second layer can each also further comprise emtricitabine.

Figure 2:
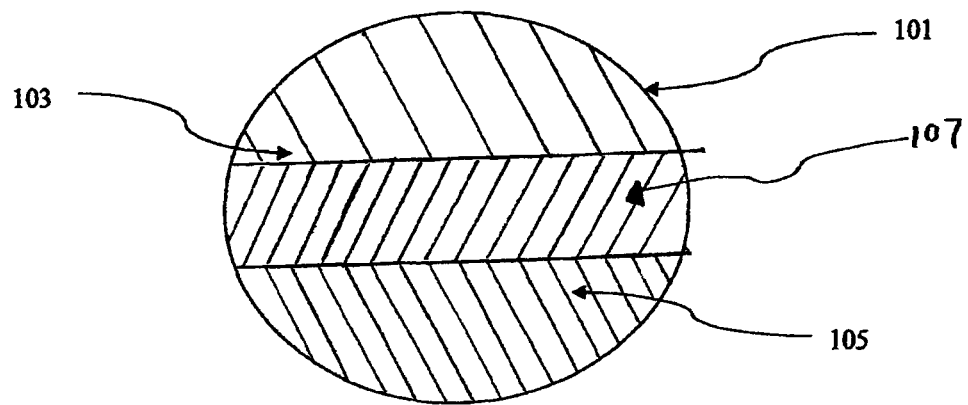
FIG. 2. Illustrates a tablet of the invention.

FIG. 2 shows a cross-section of a tablet (101) of the invention. The tablet includes a first layer (103) that comprises rilpivirine HCl. The tablet also includes a second layer (105) that comprises tenofovir DF and a third layer (107) that is inert. The first and second layer can each also further comprise emtricitabine.

Figure 3:
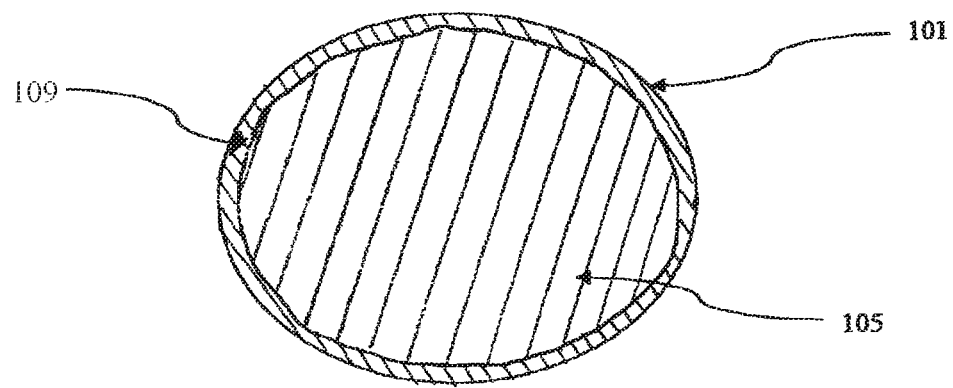
FIG. 3. Illustrates a tablet of the invention.

FIG. 3 shows a cross-section of a tablet (101) of the invention. The tablet includes a first layer (109) that comprises rilpivirine HCl and a second layer (105) that comprises tenofovir DF and emtricitabine, wherein the first layer (109) is a coating that covers the second layer (105).

COMPARATIVE EXAMPLES

Comparative Example 1

Preparation and Stability Evaluation of Co-Wet Granulation Formulation of FTC, RPV, and TDF A single co-wet granulation process was used to formulate FTC, RPV, and TDF, based on the formulation composition of TRUVADA® (emtricitibine 200 mg/tenofovir DF 300 mg) and the RPV Phase 3 clinical formulation. Because a co-wet granulation process has the benefit of ease of manufacturing it is frequently the first-choice approach to develop FDC products. The low dose of RPV and the use of excipients common in VIREAD® (tenofovir DF), TRUVADA® (emtricitibine 200 mg/tenofovir DF 300 mg), and EMTRIVA® (emtricitibine) made FTC/RPV/TDF amenable to a single-layer wet granulation process. One challenge was to maintain the stability of TDF in the presence of a surfactant.

The compositions and processing parameters of the co-wet granulation formulations evaluated are summarized in Table CE1.1 and CE1.2, respectively. Wet granulation was carried out in the presence and absence of non-ionic surfactants (poloxamer 188 and polysorbate 20).

TABLE CE1.1

| | % w/w | | | | |
|---|---|---|---|---|---|
| | 3639-182 | 3639-183 | 3866-1 | 3866-2 | 3866-22 |
| Intragranular Ingredients | | | | | |
| Rilpivirine HCl | 3.6 | 3.6 | 3.6 | 3.6 | 2.75 |
| Emtricitabine | 26.3 | 26.3 | 26.3 | 26.3 | 20.0 |
| Tenofovir disoproxil fumarate | 39.5 | 39.5 | 39.5 | 39.5 | 30.0 |
| Microcrystalline cellulose, NF (102) | 14.2 | 22.2 | 22.2 | 22.6 | 15.0 |
| Polysorbate 20 | 0.4 | 0.4 | | | |
| Poloxamer 188 | | | 0.4 | | |
| Hydroxypropyl cellulose | | 2.0 | 2.0 | 2.0 | |
| Croscarmellose sodium, NF | 2.5 | 2.5 | 2.5 | 2.5 | 3.0 |
| Lactose monohydrate (DCL-11) | 5.0 | | | | |
| Lactose monohydrate, NF, 310 Regular/Grind | | | | | 8.0 |
| Pregelatinized starch, NF | 5.0 | | | | 5.0 |
| Extragranular Ingredients | | | | | |
| Microcrystalline cellulose, NF (102) | | | | | 12.25 |
| Croscarmellose sodium, NF | 2.5 | 2.5 | 2.5 | 2.5 | 3.0 |
| Magnesium stearate, NF | 1.0 | 1.00 | 1.00 | 1.0 | 1.0 |
| Total | 100.0 | 100.0 | 100.0 | 100.0 | 100.0 |
| Total tablet weight | 760 mg | 760 mg | 760 mg | 760 mg | 1000 mg |

TABLE CE1.2

| Lot Number | Batch Size (g) | Intra-granular Amount (g) | Water for Granulation (g) | Water Addition (%) | Wet Mass-ing Time | Geometric Mean Diameter Particle Size (μm) | LOD (%) |
|---|---|---|---|---|---|---|---|
| 3639-182 | 800 | 772 | 277.5 | 36 | 8:30 | 1 | 169 | 0.74 |
| 3639-183 | 800 | 772 | 277.6 | 38 | 7:49 | 1 | 187 | 0.56 |
| 3866-1 | 800 | 772 | 275.0 | 36 | 8:27 | 1 | 226 | 0.49 |
| 3866-2 | 800 | 772 | 275.0 | 36 | 8:00 | 1 | 204 | 0.56 |
| 3866-22 | 800 | 670 | 175.0 | 41 | 5:19 | 0 | 207 | 0.96 |

Figure 7:
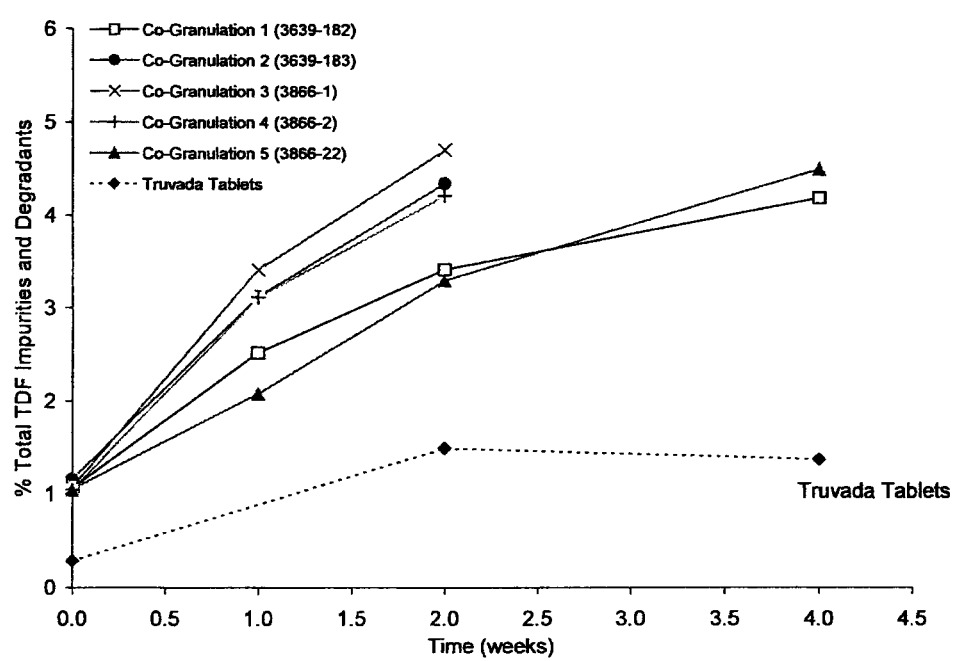
FIG. 7. Illustrates the percent total TDF degradation over time measured in Comparative Example 1.

The uncoated tablets were packaged with 3 g of silica gel desiccant and stored in 50° C. and 40° C./75% RH stability chambers to stress the tablet samples and accelerate the degradation rate to give an indication of longer term stability of the tablets under ambient conditions (25° C./60% RH). Preformulation studies have shown that TDF undergoes hydrolysis in an aqueous solution and to a smaller degree in the solid state after exposure to humidity and heat. The degradation products are mono-POC PMPA, isopropanol, carbon dioxide, and formaldehyde. The rate and extent of degradation of TDF in the co-wet granulation formulations was significantly higher than in commercial TRUVADA® (emtricitabine 200 mg/tenofovir DF 300 mg) tablets. The total TDF-related impurities and degradation products increased to more than 4% after 2 weeks at 50° C. Various attempts to improve the chemical stability of TDF in the co-wet granulation formulations by removing surfactant or by increasing the concentrations of microcrystalline cellulose and pregelatinized starch failed to improve formulation stability. These results demonstrate that a co-wet granulation process is not ideal for human clinical use. The stability data at 50° C. are summarized in FIG. 7. All formulations show a much greater degradation rate of TDF than in TRUVADA® (emtricitabine 200 mg/tenofovir DF 300 mg) tablets.

As illustrated below in Example 6 representative tablets of the invention overcome the problem of reduced TDF stability present in the co-wet formulation above.

Comparative Example 2

Preparation of Formulation 1

Formulation 1 was manufactured by blending FTC, RPV, and TDF together with excipients then dry granulating them together using a dry granulation process, which employs a roller compactor and mill. The granules were blended with extragranular excipients and compressed into tablet cores, which were then film-coated. The composition parameters for the co-dry granulation formulation (Formulation 1) are summarized in Table CE2.1

TABLE CE2.1

| Ingredient | Unit Formula for FTC/RPV/TDF Tablets (mg/tablet) |
|---|---|
| Emtricitabine | 200.0 |
| Rilpivirine Hydrochloride | 27.5[a] |
| Tenofovir Disoproxil Fumarate | 300.0[b] |
| Microcrystalline Cellulose | 218.4 |
| Croscarmellose Sodium | 85.0 |
| Magnesium Stearate | 19.1 |
| Tablet Core Weight | 850.0 |
| Film Coat Components | |
| Opadry II Purple 33G100000 | 25.5 |
| Total Tablet Weight | 875.5 |

[a]Equivalent to 25.0 mg of rilpivirine free base
[b]Equivalent to 245 mg of tenofovir disoproxil Comparative Example 3

Preparation of Formulation 2

Formulation 2 was prepared using two separate granulation processes in which rilpivirine HCl was wet granulated by a fluid-bed granulation process and emtricitabine and tenofovir DF were co-granulated in a high shear wet granulation process. This formulation was designed to use the intragranular rilpivirine HCl formulation and fluid-bed granulation process used to prepare the RPV tablet that is now being evaluated in Phase 3 clinical trials. The emtricitabine/tenofovir DF powder blend was produced using the process and the intragranular composition used in the manufacture of TRUVADA® (emtricitibine 200 mg/tenofovir DF 300 mg). The two granulations were then blended together with lubricant, compressed into a single layer tablet, and then film-coated. The composition parameters of Formulation 2 are summarized in Table CE3.1

TABLE CE3.1

| Ingredient | Unit Formula for FTC/RPV/TDF Tablets (mg/tablet) |
|---|---|
| Emtricitabine | 200.0 |
| Rilpivirine Hydrochloride | 27.5[a] |
| Tenofovir Disoproxil Fumarate | 300.0[b] |
| Microcrystalline Cellulose | 212.7 |
| Lactose Monohydrate | 135.1 |
| Povidone | 3.3 |
| Pregelatinized Starch | 50.0 |
| Polysorbate 20 | 0.4 |
| Croscarmellose Sodium | 61.1 |
| Magnesium Stearate | 10.0 |
| Tablet Core Weight | 1000.0 |
| Film Coat Components | |
| Opadry II Purple 33G100000 | 30.0 |
| Total Tablet Weight | 1030.0 |

[a]Equivalent to 25.0 mg rilpivirine free base.
[b]Equivalent to 245 mg of tenofovir disoproxil Comparative Example 4

Stability of Formulation 1 and Formulation 2

Figure 8:
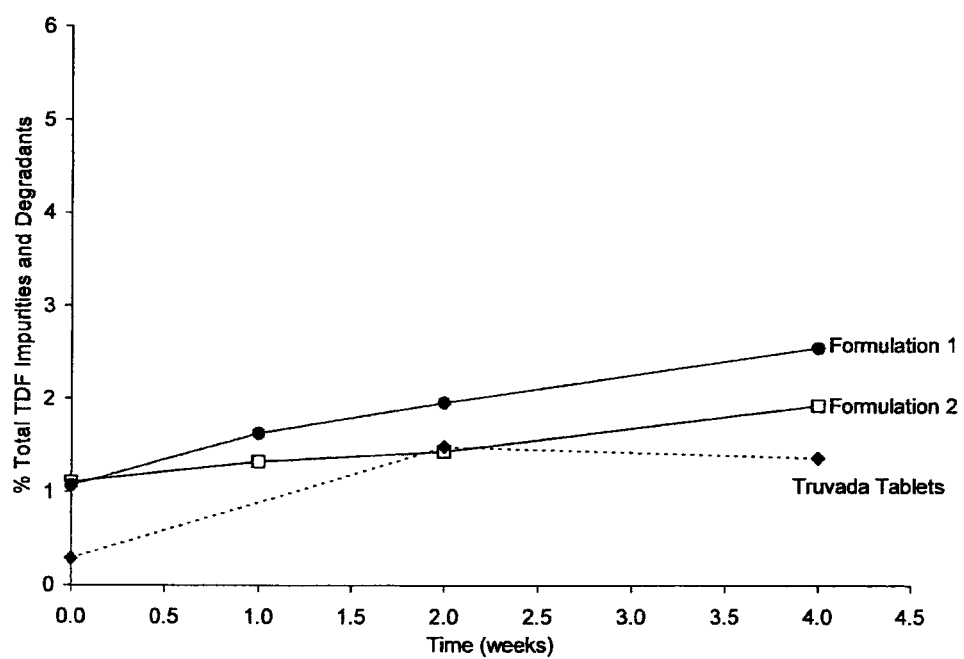
FIG. 8. Illustrates the percent total TDF degradation over time measured in Comparative Example 4.

Identity and strengths of the APIs and degradation products were determined using an HPLC method, which employed a 4.6×250-mm C-12 column (4-μm particle size) for chromatographic separation by reversed-phase chromatography using a mobile phase consisting of ammonium acetate buffer and acetonitrile with gradient elution over approximately 60 minutes. Composite samples of 10 tablets were dissolved and diluted to final concentrations of approximately 0.08 mg/mL RPV, 0.64 mg/mL FTC, and 0.96 mg/mL TDF with a 4:3:3 pH 3 phosphate buffer:acetonitrile:methanol solution. The strength and degradation product content of FTC, RPV, and TDF were determined by HPLC using area normalization and external reference standards at a wavelength of 262 nm. The stability data for 30 count tablets stored at 40° C./75% RH in induction sealed bottles containing 3 g silica gel desiccant are summarized in FIG. 8.

In Comparative Example 5 below the bioavailabilies of Formulation 1 and Formulation 2 from Comparative Examples 2 and 3 were assessed. Formulations 1 and 2 both failed to demonstrate bioequivalence for rilpivirine with significantly higher area under the curve (AUC) and Cmax levels than those obtained with the rilpivirine tablet that is now being evaluated in clinical trials. Accordingly, the human plasma concentration of rilpivirine produced by Formulation 1 and by Formulation 2 is not equivalent to the plasma concentration of rilpivirine produced in the current clinical trials. A representative tablet of the invention did demonstrate the beneficial property of providing a plasma concentration of rilpivirine that is equivalent to the plasma level produced in the current clinical trials (See Example 5 below).

Comparative Example 5

Bioavailability of Formulation 1 and Formulation 2

A clinical study was conducted to assess the bioavailability and bioequivalence of Formulations 1 and 2 relative to co-administration of the individual components, with all treatments administered in the fed state. Formulations 1 and 2 both failed to demonstrate bioequivalence for rilpivirine with significantly higher area under the curve (AUC) and Cmax levels than those obtained with the rilpivirine tablet that is now being evaluated in Phase 3 clinical trials. In contrast, both emtricitabine and tenofovir AUC and $C_{max}$ levels from Formulations 1 and 2 were bioequivalent to the commercial formulations of EMTRIVA® (Emtracitabine) and VIREAD® (tenofovir DF), respectively. The significantly higher exposure levels of rilpivirine observed from Formulations 1 and 2 in the bioequivalence study may be due to the direct physicochemical interactions between rilpivirine HCl and either emtricitabine or tenofovir DF. These results suggest that the formulation and the manufacturing process required significant modifications to achieve the desired rilpivirine exposures.

| RPV PK Parameter | Test | Reference | % GMR (90% CI) |
|---|---|---|---|
| Formulation 1 | | | |
| $C_{max}$ | 166 (25%) | 109 (28%) | 154 (147, 161) |
| $AUC_{last}$ | 3685 (22%) | 2742 (29%) | 136 (130, 143) |
| $AUC_{inf}$ | 4005 (23%) | 3021 (32%) | 135 (129, 142) |
| Formulation 2 | | | |
| $C_{max}$ | 163 (24%) | 109 (28%) | 151 (144, 158) |
| $AUC_{last}$ | 3659 (24%) | 2742 (29%) | 135 (129, 141) |
| $AUC_{inf}$ | 3983 (24%) | 3021 (32%) | 134 (128, 141) |

$C_{max}$: ng/mL,
AUC: ng * hr/mL

EXAMPLES

Example 1

Synthesis of a Representative Bilayer Tablet of the Invention

Figure 4:
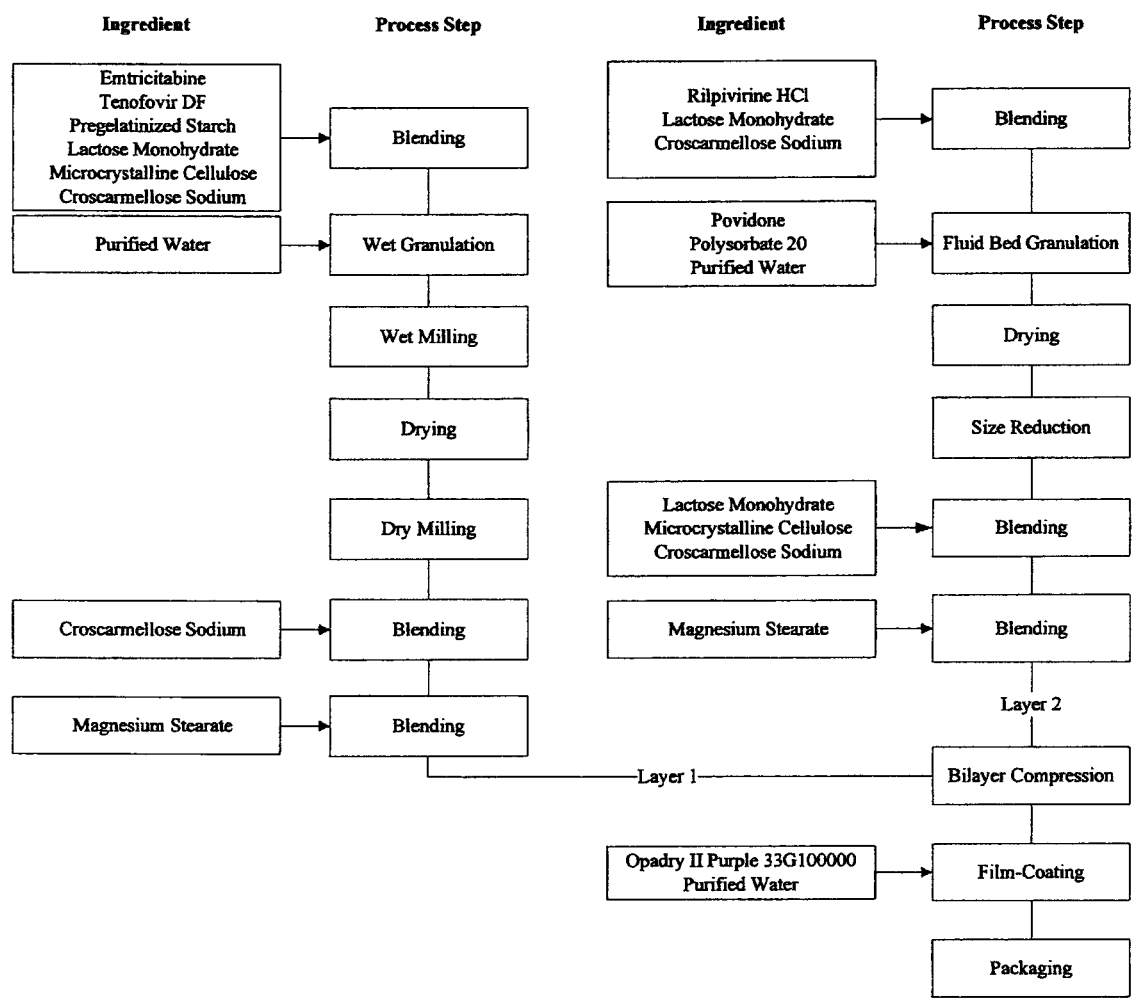
FIG. 4. Is a flow diagram that illustrates the preparation of a representative tablet of the invention that is described in Example 1.

In one embodiment of the invention the manufacturing procedure can be broken down into multiple segments: fluid-bed granulation and drying of rilpivirine HCl, high shear wet granulation of emtricitabine and tenofovir DF, milling and blending of each granulation, bilayer tableting, film-coating of the bulk tablets, and packaging. The stepwise procedure is detailed below. To accommodate the equipment capacities, the in-process product may be granulated and dried in multiple portions, which are then combined prior to the final milling and blending steps. As illustrated in FIG. 4, a representative tablet of the invention can be prepared as follows.

Fluid-Bed Granulation of Rilpivirine HCl

1) Weigh rilpivirine HCl and the excipients (lactose monohydrate and croscarmellose sodium). Correct the weight of rilpivirine HCl based on the drug content factor, with a concomitant reduction in the weight of lactose monohydrate.

2) Weigh purified water, polysorbate 20, and povidone. Mix in 2 steps in a stainless steel vessel to form the granulation binder fluid. First, add povidone, then add polysorbate 20 and mix until fully dissolved.

3) Add rilpivirine HCl, lactose monohydrate, and croscarmellose sodium to the fluid-bed granulator/dryer and fluidize the bed to pre-mix the components.

4) Spray the entire volume of binder solution while maintaining powder bed fluidization.

5) After solution addition, dry the granules in the fluid-bed granulator/dryer to a suitable moisture content as determined by loss on drying (LOD).

Milling and Blending of Rilpivirine Blend

6) Transfer the dried granulation through a mill for particle size reduction.

7) Add the dried, milled granules as well as extragranular lactose monohydrate, microcrystalline cellulose, and croscarmellose sodium and blend in a blender.

8) Add extragranular magnesium stearate and blend.

Wet Granulation of Emtricitabine/Tenofovir DF

9) Weigh emtricitabine, tenofovir DF, and excipients (pregelatinized starch, croscarmellose sodium, lactose monohydrate, microcrystalline cellulose, and magnesium stearate). Correct the weight of tenofovir DF and emtricitabine based on the drug content factor and correspondingly adjust the weight of lactose monohydrate.

10) Add emtricitabine, tenofovir DF, and the intragranular excipients (pregelatinized starch, croscarmellose sodium, microcrystalline cellulose, and lactose monohydrate) to the high shear granulator/mixer and blend with the impeller set to low speed.

11) Add water to the dry blend while mixing with the impeller (mixer) and granulator (chopper) to form the wet granulation. After water addition, wet mass to complete the granule formation.

12) Mill the wet granulated material.
Fluid-Bed Drying
13) Transfer the wet granulation to the fluid bed dryer and dry the granules to suitable moisture content as determined by loss on drying (LOD).
Milling and Blending of Emtricitabine/Tenofovir DF Blend
14) Transfer the dried granules and the extragranular excipient (croscarmellose sodium) through a mill for particle size reduction.
15) Blend the mixture.
16) Add magnesium stearate to the mixture and blend.
Tableting
17) Compress the emtricitabine/tenofovir DF final powder blend followed by the rilpivirine final powder blend to target weight and hardness on a bilayer tablet press.
Film-Coating
18) Film-coat the uncoated tablet cores with an aqueous suspension of Opadry II Purple 33G100000 to achieve the target weight gain.

Example 2

Synthesis of a Representative Trilayer Tablet of the Invention

Figure 5:
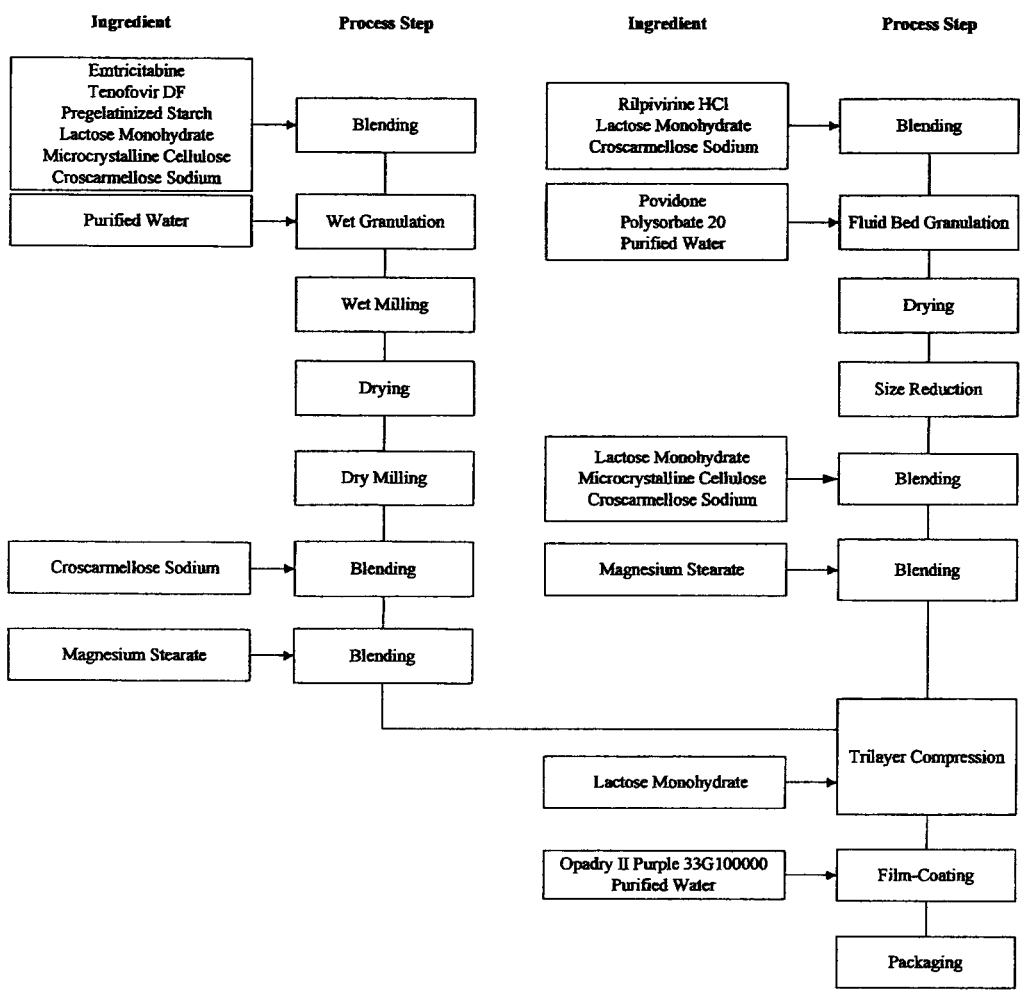
FIG. 5. Is a flow diagram that illustrates the preparation of a representative tablet of the invention that is described in Example 2.

In one embodiment of the invention the manufacturing can be broken down into multiple segments: fluid-bed granulation and drying of rilpivirine HCl, high shear wet granulation of emtricitabine and tenofovir DF, milling and blending of each granulation, trilayer tableting, film-coating of the bulk tablets, and packaging. The stepwise procedure is detailed below. To accommodate the equipment capacities, the in-process product may be granulated and dried in multiple portions, which are then combined prior to the final milling and blending steps. As illustrated in FIG. 5, a representative tablet of the invention can be prepared as follows.
Fluid-Bed Granulation of Rilpivirine HCl
1) Weigh rilpivirine HCl and the excipients (lactose monohydrate and croscarmellose sodium). Correct the weight of rilpivirine HCl based on the drug content factor, with a concomitant reduction in the weight of lactose monohydrate.
2) Weigh purified water, polysorbate 20, and povidone. Mix in 2 steps in a stainless steel vessel to form the granulation binder fluid. First, add povidone, then add polysorbate 20 and mix until fully dissolved.
3) Add rilpivirine HCl, lactose monohydrate, and croscarmellose sodium to the fluid-bed granulator/dryer and fluidize the bed to pre-mix the components.
4) Spray the entire quantity of binder solution while maintaining powder bed fluidization to ensure uniform granule growth.
5) After solution addition, dry the granules in the fluid-bed granulator/dryer to a suitable moisture content as determined by loss on drying (LOD).
Milling and Blending of Rilpivirine Blend
6) Transfer the dried granulation through a mill for particle size reduction.
7) Add the dried, milled granules as well as extragranular lactose monohydrate, microcrystalline cellulose, and croscarmellose sodium and blend in a blender.
8) Add extragranular magnesium stearate and blend.
Wet Granulation of Emtricitabine/Tenofovir DF
9) Weigh emtricitabine, tenofovir DF, and excipients (pregelatinized starch, croscarmellose sodium, lactose monohydrate, microcrystalline cellulose, and magnesium stearate). Correct the weight of tenofovir DF and emtricitabine based on the drug content factor and correspondingly adjust the weight of lactose monohydrate.
10) Add emtricitabine, tenofovir DF, and the intragranular excipients (pregelatinized starch, croscarmellose sodium, microcrystalline cellulose, and lactose monohydrate) to the high shear granulator/mixer and blend with the impeller set to low speed.
11) Add water to the dry blend while mixing with the impeller (mixer) and granulator (chopper) to form the wet granulation. After water addition, wet mass to complete the granule formation.
12) Mill the wet granulated material.
Fluid-Bed Drying
13) Transfer the wet granulation to the fluid bed dryer and dry the granules to suitable moisture content as determined by loss on drying (LOD).
Milling and Blending of Emtricitabine/Tenofovir DF Blend
14) Transfer the dried granules and the extragranular excipient (croscarmellose sodium) through a mill for particle size reduction.
15) Blend the mixture.
16) Add magnesium stearate to the mixture and blend.
Tableting
17) Compress the emtricitabine/tenofovir DF final powder blend followed by the rilpivirine final powder blend to target weight and hardness on a trilayer tablet press with lactose monohydrate or microcrystalline cellulose as the middle layer.
Film-Coating
18) Film-coat the uncoated tablet cores with an aqueous suspension of Opadry II Purple 33G100000 to achieve the target weight gain.

Example 3

Synthesis of a Representative Bilayer Tablet of the Invention

Figure 6:
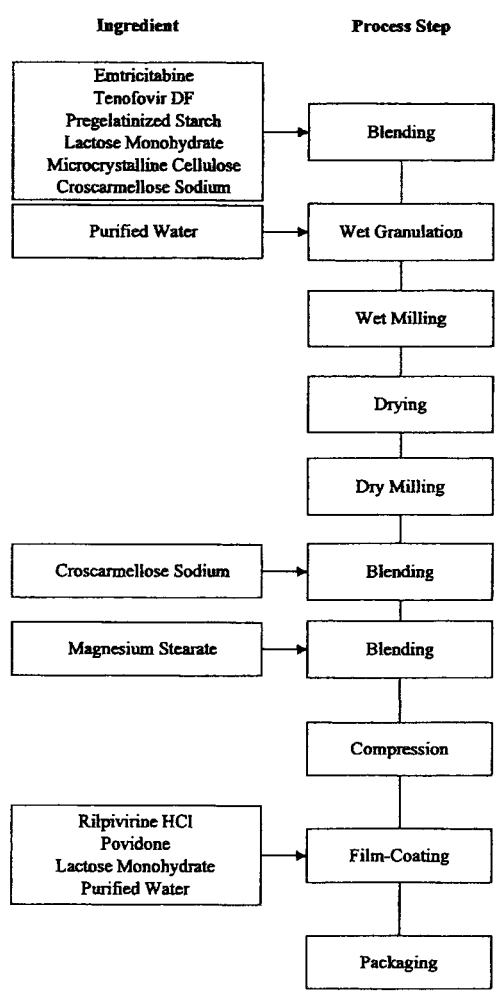
FIG. 6. Is a flow diagram that illustrates the preparation of a representative tablet of the invention that is described in Example 3.

To accommodate the equipment capacities, the in-process product may be granulated and dried in multiple portions, which are then combined prior to the final milling and blending steps. As illustrated in FIG. 6, a representative tablet of the invention can be prepared as follows.
Wet Granulation of Emtricitabine/Tenofovir DF
1) Weigh emtricitabine, tenofovir DF, and excipients (pregelatinized starch, croscarmellose sodium, lactose monohydrate, microcrystalline cellulose, and magnesium stearate). Correct the weight of tenofovir DF and emtricitabine based on the drug content factor and correspondingly adjust the weight of lactose monohydrate.
2) Add emtricitabine, tenofovir DF, and the intragranular excipients (pregelatinized starch, croscarmellose sodium, microcrystalline cellulose, and lactose monohydrate) to the high shear granulator/mixer and blend with the impeller set to low speed.
3) Add water to the dry blend while mixing with the impeller (mixer) and granulator (chopper) to form the wet granulation. After water addition, wet mass to complete the granule formation.
4) Mill the wet granulated material.
Fluid-Bed Drying
5) Transfer the wet granulation to the fluid bed dryer and dry the granules to suitable moisture content as determined by loss on drying (LOD).

Milling and Blending of Emtricitabine/Tenofovir DF Blend

6) Transfer the dried granules and the extragranular excipient (croscarmellose sodium) through a mill for particle size reduction.
7) Blend the mixture.
8) Add magnesium stearate to the mixture and blend.

Tableting

9) Compress the emtricitabine/tenofovir DF final powder blend to target weight and hardness on a single layer tablet press RPV Film-Coating 10) Prepare a solution or suspension of RPV in an organic solvent or aqueous media. The solution or suspension can contain additional excipients such as povidone, polyethylene glycol, hypromellose, lactose monohydrate, and/or a wetting agent to aid in the adhesion of the film-coat to the tablet surface.
11) Film-coat the uncoated tablet cores with the solution/suspension of polymer and rilpivirine HCl to achieve the target weight gain for potency.

Example 4

Preparation of Representative Tablets of the Invention

Bilayer formulations were investigated where one layer contained rilpivirine HCl (hereafter designated as the rilpivirine layer) and the other layer contained emtricitabine and tenofovir DF. This approach was employed to minimize any potential physicochemical interactions between rilpivirine HCl and emtricitabine and tenofovir DF. The bilayer formulation approach involved two separate granulation processes in which rilpivirine HCl was wet granulated using a fluid-bed granulation process and emtricitabine and tenofovir DF were co-granulated using a high shear wet granulation process. The two granulations were physically separated by compressing the two blends into a bilayer tablet (Formulations 3 and 4). The quantitative compositions for Formulations 3 and 4 are listed in Table 4.1 and Table 4.2 respectively. While Formulations 3 and 4 utilized the same manufacturing process, the formulation composition of the rilpivirine HCl granulation in each of the formulations differed in the relative proportion of the excipients used.

TABLE 4.1

Quantitative Composition of Formulation 3 Tablets

| Ingredient | Unit Formula for FTC/RPV/TDF Tablets (mg/tablet) |
|---|---|
| RPV Layer | |
| Rilpivirine HCl | 27.5[a] |
| Microcrystalline Cellulose | 60.0 |
| Lactose Monohydrate | 189.8 |
| Povidone | 3.3 |
| Polysorbate 20 | 0.4 |
| Croscarmellose Sodium | 16.1 |
| Magnesium Stearate | 3.0 |
| Total Layer Weight | 300.0 |
| FTC/TDF Layer | |
| Emtricitabine | 200.0 |
| Tenofovir DF | 300.0[b] |
| Microcrystalline Cellulose | 150.0 |
| Lactose Monohydrate | 80.0 |

TABLE 4.1-continued

Quantitative Composition of Formulation 3 Tablets

| Ingredient | Unit Formula for FTC/RPV/TDF Tablets (mg/tablet) |
|---|---|
| Pregelatinized Starch | 50.0 |
| Croscarmellose Sodium | 60.0 |
| Magnesium Stearate | 10.0 |
| Total Layer Weight | 850.0 |
| Film Coat Components | |
| Opadry II Purple 33G100000 | 34.5 |
| Total Tablet Weight | 1184.5 |

[a]Equivalent to 25.0 mg rilpivirine free base.
[b]Equivalent to 245 mg of tenofovir disoproxil

TABLE 4.2

Quantitative Composition of Formulation 4 Tablets

| Ingredient | Unit Formula for FTC/RPV/TDF Tablets (mg/tablet) |
|---|---|
| RPV Layer[a] | |
| Rilpivirine HCl | 27.5[a] |
| Microcrystalline Cellulose | 45.0 |
| Lactose Monohydrate | 134.3 |
| Povidone | 3.3 |
| Polysorbate 20 | 0.4 |
| Croscarmellose Sodium | 12.4 |
| Magnesium Stearate | 2.3 |
| Total Layer Weight | 225.0 |
| FTC/TDF Layer | |
| Emtricitabine | 200.0 |
| Tenofovir DF | 300.0[b] |
| Microcrystalline Cellulose | 150.0 |
| Lactose Monohydrate | 80.0 |
| Pregelatinized Starch | 50.0 |
| Croscarmellose Sodium | 60.0 |
| Magnesium Stearate | 10.0 |
| Total Layer Weight | 850.0 |
| Film Coat Components | |
| Opadry II Purple 33G100000 | 32.3 |
| Total Tablet Weight | 1107.3 |

[a]Equivalent to 25.0 mg rilpivirine free base.
[b]Equivalent to 245 mg of tenofovir disoproxil Formulations 3 and 4 were designed to minimize the formulation and manufacturing process differences between the fixed-dose combination tablets and the formulation currently in clinical trials by using the existing intragranular RPV formulation and fluid-bed granulation process. In addition, the rilpivirine HCl was separated from emtricitabine and tenofovir DF. This was accomplished through a bilayer compression process to produce the tablets. The emtricitabine/tenofovir DF powder blend was produced by the same manufacturing process and using the same intragranular composition for TRUVADA® (emtricitibine 200 mg/tenofovir DF 300 mg). The weight disparity between rilpivirine and emtricitabine/tenofovir DF layers required dilution of the rilpivirine HCl granulation to ensure a robust tablet manufacturing process. The layer weights in Formulations 3 and 4 were accommodated by adjusting the concentrations of the excipients in the rilpivirine layer with microcrystalline cellulose, lactose monohydrate, croscarmellose sodium, and magnesium stearate.

Example 5

Bioavailability of Formulations 3 and 4

This study evaluated the bioequivalence of Formulation 3 from Example 4 to coadministration of the three individual dosage forms (FTC+RPV+TDF, Reference)

A randomized, single-dose, open-label, Phase 1 study in healthy adults under fed conditions. Serial blood samples were obtained over 192 hours following oral administration of each treatment and PK parameters calculated. Formulation bioequivalence was assessed by 90% confidence intervals (CI) for the ratio of geometric least square means (GMR) for $C_{max}$, $AUC_{last}$ and $AUC_{inf}$ for each drug of the Test versus Reference treatment.

Results:

36 subjects enrolled and 34 completed the study. All treatments were generally well tolerated; most adverse events seen were mild in severity. The arithmetic mean and the geometric mean ratio (GMR), along with the 90% confidence interval, of the PK parameters are presented below.

| PK Parameter | | Reference | % GMR (90% Confidence Interval) |
|---|---|---|---|
| | Formulation 3 | | |
| RPV | | | |
| $C_{max}$ | 110 | 95 | 116 (108, 124) |
| $AUC_{last}$ | 2855 | 2467 | 116 (109, 123) |
| $AUC_{inf}$ | 3167 | 2739 | 116 (109, 124) |
| FTC | | | |
| $C_{max}$ | 1714 | 1625 | 105 (100, 111) |
| $AUC_{last}$ | 9361 | 9366 | 100 (98, 102) |
| $AUC_{inf}$ | 9581 | 9595 | 100 (98, 102) |
| TFV | | | |
| $C_{max}$ | 315 | 284 | 111 (104, 118) |
| $AUC_{last}$ | 3053 | 2989 | 102 (99, 105) |
| $AUC_{inf}$ | 3264 | 3200 | 102 (99, 105) |
| | Formulation 4 | | |
| RPV | | | |
| $C_{max}$ | 115 | 95 | 122 (114, 130) |
| $AUC_{last}$ | 2889 | 2467 | 117 (110, 124) |
| $AUC_{inf}$ | 3211 | 2739 | 117 (110, 125) |
| FTC | | | |
| $C_{max}$ | 1754 | 1625 | 108 (103, 113) |
| $AUC_{last}$ | 9433 | 9366 | 101 (99, 102) |
| $AUC_{inf}$ | 9646 | 9595 | 101 (98, 103) |
| TFV | | | |
| $C_{max}$ | 323 | 284 | 114 (107, 121) |
| $AUC_{last}$ | 3110 | 2989 | 104 (101, 107) |
| $AUC_{inf}$ | 3333 | 3200 | 104 (101, 107) |

$C_{max}$: ng/mL,
AUC: ng * hr/mL

Formulation 3 was found to produce human plasma concentrations of each of the three agents that were equivalent to the plasma concentrations produced by the administration of the individual agents. Formulation 4 from Example 4 did not produce human plasma concentrations of each of the three agents that were equivalent to the plasma concentrations produced by the administration of the individual agents.

Formulation 3 and Formulation 4 differ in the weight of extragranular excipients and in the amount of croscarmellose sodium present. The bioequivalent formulation (Formulation 3) has significantly higher (38%) amounts of extragranular excipients (microcrystalline cellulose and lactose monohydrate) and croscarmellose sodium in the rilpivirine layer than Formulation 4. Laboratory data showed that the intrinsic dissolution rate of rilpivirine was increased in the presence of emtricitabine and/or tenofovir DF suggesting an increased solubility could contribute to a higher rilpivirine bioavailability when co-formulated with emtricitabine and tenofovir DF. It may be postulated that the higher amounts of diluents in the rilpivirine layer of Formulation 3 that was bioequivalent to the rilpivirine single agent reference tablet could have served to lessen the extent of contact and interactions between rilpivirine and emtricitabine and/or tenofovir DF and achieve bioequivalence.

Figure 9:
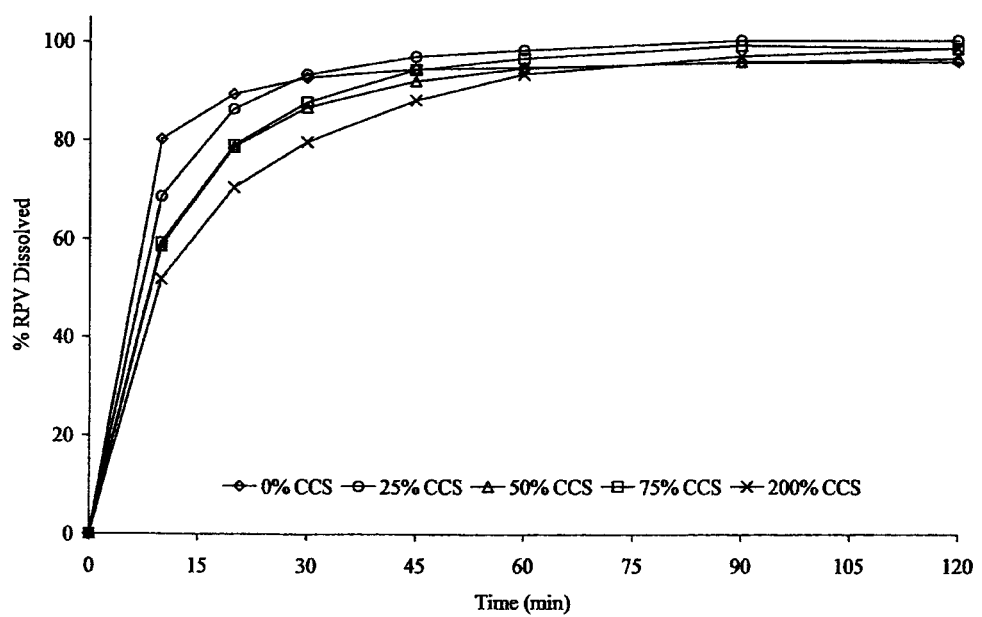
FIG. 9. Illustrates the percent RPV dissolved as measured in Example 5.

In addition, the higher amount of croscarmellose sodium, a superdisintegrant, leads to faster layer disintegration and separation of the rilpivirine layer from the emtricitabine/tenofovir DF layer minimizing any potential interactions between rilpivirine with emtricitabine and/or tenofovir DF. The concentration of croscarmellose sodium, a basifying excipient, in the rilpivirine layer also had an unexpected effect on the rilpivirine dissolution rate. Higher concentrations of this superdisintegrant, unexpectedly decreased the dissolution rate as shown in FIG. 9. This is possibly due to the basifying nature of this excipient.

Example 6

Stability of Components of Formulation 3

Identity and strengths of the APIs and degradation products were determined using an HPLC method, which employed a 4.6×250-mm C-12 column (4-μm particle size) for chromatographic separation by reversed-phase chromatography using a mobile phase consisting of ammon2ium acetate buffer and acetonitrile with gradient elution over approximately 60 minutes. Composite samples of 10 tablets were dissolved and diluted to final concentrations of approximately 0.08 mg/mL RPV, 0.64 mg/mL FTC, and 0.96 mg/mL TDF with a 4:3:3 pH 3 phosphate buffer:acetonitrile:methanol solution. The strength and degradation product content of FTC, RPV, and TDF were determined by HPLC using area normalization and external reference standards at a wavelength of 262 nm. The stability data for 30 count tablets stored at 40° C./75% RH in induction sealed bottles containing 3 g silica gel desiccant are summarized in the table below and demonstrate acceptable chemical stability under accelerated storage conditions.

| | Lot Number | | |
|---|---|---|---|
| Time Point | 1 | 2 | 3 |
| | Rilpivirine Strength (%)/Total Degradation Content (%) | | |
| 0 month | 100.2/0.0 | 100.8/0.0 | 99.5/0.0 |
| 1 month | 100.4/0.0 | 100.8/0.0 | 99.6/0.0 |
| 3 months | 100.3/0.0 | 99.5/0.0 | 99.2/0.0 |

-continued

| Time Point | Lot Number | | |
|---|---|---|---|
| | 1 | 2 | 3 |
| Emtricitabine Strength (%)/Total Degradation Content (%) | | | |
| 0 month | 99.1/0.0 | 99.1/0.0 | 102.6/0.0 |
| 1 month | 99.5/0.0 | 100.2/0.0 | 102.6/0.0 |
| 3 months | 98.5/0.0 | 97.1/0.1 | 100.5/0.1 |
| Tenofovir Disoproxil Fumarate Strength (%)/ Total Degradation Content (%) | | | |
| 0 month | 101.0/0.6 | 102.1/0.7 | 102.0/0.8 |
| 1 month | 101.1/0.7 | 102.7/0.9 | 101.5/1.0 |
| 3 months | 100.5/0.9 | 99.9/1.2 | 99.7/1.3 |

Example 7

Stability of Components of Formulation 4

The stability data for 30 count tablets stored at 40° C./75% RH in induction sealed bottles containing 3 g silica gel desiccant are summarized in the table below and demonstrate acceptable chemical stability under accelerated storage conditions comparable to Formulation 3.

| Time Point | Lot Number | | |
|---|---|---|---|
| | 1 | 2 | 3 |
| Rilpivirine Strength (%)/Total Degradation Content (%) | | | |
| 0 month | 100.3/0.2 | 99.4/0.1 | 100.7/0.1 |
| 1 month | 100.9/0.2 | 99.1/0.1 | 97.6/0.1 |
| Emtricitabine Strength (%)/Total Degradation Content (%) | | | |
| 0 month | 98.0/0.0 | 103.1/0.0 | 100.3/0.0 |
| 1 month | 99.6/0.0 | 104.4/0.0 | 100.8/0.0 |
| Tenofovir Disoproxil Fumarate Strength (%)/ Total Degradation Content (%) | | | |
| 0 month | 101.7/0.6 | 99.4/0.7 | 102.6/0.8 |
| 1 month | 103.2/0.7 | 100.2/0.9 | 102.7/0.9 |

Example 8

Example Food Effect

Formulation 3 was evaluated in a comparative bioavailability study to assess the effect of food on the exposure of rilpivirine HCl when dosed in the reference group as three individual tablets containing emtricitabine, rilpivirine HCl, and tenofovir DF.

The "fed" state or "fed conditions" refers to administering the study drugs within 5 minutes of completing a standardized meal (breakfast). Subjects were restricted from food consumption for approximately 4 hours after dosing. A meal (standardized lunch) was provided to subjects after the 4-hour postdose blood draw. All meals and/or snacks were standardized for all subjects and were to be similar in calorie and fat content and taken at approximately the same time each day. The standardized breakfast on dosing days contained approximately 400 calories (kcal) and approximately 13 g of fat.

The "fasted" state refers to administering the study drugs in the absence of food. Subjects were fasted overnight, administered the study drugs, and then restricted from food consumption for approximately 4 hours after dosing. A meal (standardized lunch) was provided to subjects after the 4-hour postdose blood draw.

A comparison of the mean values of the pharmacokinetic parameters are presented below along with the mean values of the Reference group under fed conditions. The AUC values for Formulation 3 under the fasted state are identical to the Reference group under fed conditions. The Reference group under the fasted state shows a 26% reduction in the AUC values as compared to the fed conditions.

| PK Parameter | Reference Fed (n = 34) | Formulation 3 Fasted (n = 15) | Reference Fasted (n = 15) |
|---|---|---|---|
| RPV | | | |
| $C_{max}$ | 95 | 77 | 63 |
| $AUC_{last}$ | 2467 | 2510 | 1960 |
| $AUC_{inf}$ | 2739 | 2730 | 2170 |

$C_{max}$: ng/mL,
AUC: ng * hr/mL

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A tablet comprising a first layer and a second layer, wherein the first layer consists of 27.5 mg rilpivirine HCl, 60.0 mg microcrystalline cellulose, 189.8 mg lactose monohydrate, 3.3 mg povidone, 0.4 mg polysorbate 20, 16.1 mg croscarmellose sodium, and 3.0 mg magnesium stearate;
    and the second layer consists of 200.0 mg emtricitabine, 300.0 mg tenofovir disoproxil fumarate, 150.0 mg microcrystalline cellulose, 80.0 mg lactose monohydrate, 50.0 mg pregelatinized starch, 60.0 mg croscarmellose sodium, and 10.0 mg magnesium stearate.

2. A tablet comprising a first layer, a second layer, and a third layer that is between and that separates the first layer and the second layer, wherein the first layer consists of 27.5 mg rilpivirine HCl, 60.0 mg microcrystalline cellulose, 189.8 mg lactose monohydrate, 3.3 mg povidone, 0.4 mg polysorbate 20, 16.1 mg croscarmellose sodium, and 3.0 mg magnesium stearate;
    the second layer consists of 200.0 mg emtricitabine, 300.0 mg tenofovir disoproxil fumarate, 150.0 mg microcrystalline cellulose, 80.0 mg lactose monohydrate, 50.0 mg pregelatinized starch, 60.0 mg croscarmellose sodium, and 10.0 mg magnesium stearate;
    and the third layer comprises 150±8.0 mg of microcrystalline cellulose or lactose monohydrate, or a mixture thereof.

3. A tablet having a first layer that consists of 27.5 mg rilpivirine HCl, 60.0 microcrystalline cellulose, 189.8 mg lactose monohydrate, 3.3 mg povidone, 0.4 mg polysorbate 20, 16.1 mg croscarmellose sodium, and 3.0 mg magnesium stearate;
    a second layer that consists of 200.0 mg emtricitabine, 300.0 mg tenofovir DF, 150.0 mg microcrystalline cellulose, 80.0 mg lactose monohydrate, 50.0 mg pregelatinized starch, 60.0 mg croscarmellose sodium, and 10.0 mg magnesium stearate;
    and 34.5 mg of a film coating.

4. The tablet of claim 1, wherein the tablet further comprises a film coating.

5. The tablet of claim 4, wherein the film coating comprises a hydrophilic polymer material.

* * * * *

UNITED STATES PATENT AND TRADEMARK OFFICE
CERTIFICATE OF CORRECTION

PATENT NO. : 10,857,102 B2
APPLICATION NO. : 13/988072
DATED : December 8, 2020
INVENTOR(S) : Reza Oliyai, Lauren Wiser and Mark Menning Page 1 of 1

It is certified that error appears in the above-identified patent and that said Letters Patent is hereby corrected as shown below:

On the Title Page

Column 2, (Other Publications), Line 15, delete "Ecudorian" and insert -- Ecuadorian --, Column 2, (Abstract), Line 2, delete "tenofivir" and insert -- tenofovir --, In the Claims Column 24, Line 58, Claim 3, delete "60.0" and insert -- 60.0 mg --.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*